US012370058B2

United States Patent
McLean et al.

(10) Patent No.: US 12,370,058 B2
(45) Date of Patent: Jul. 29, 2025

(54) BELT DRIVEN EXPANDABLE INTERBODY FUSION DEVICE

(71) Applicant: SPINE WAVE, INC., Shelton, CT (US)

(72) Inventors: Scott McLean, Sandy Hook, CT (US); Haibo Fan, Woodbridge, CT (US); Emily Anne Pugh, Stamford, CT (US); Phillip T. Harkawik, Fairfield, CT (US)

(73) Assignee: SPINE WAVE, INC., Shelton, CT (US)

( * ) Notice: Subject to any disclaimer, the term of this patent is extended or adjusted under 35 U.S.C. 154(b) by 308 days.

(21) Appl. No.: 18/130,074

(22) Filed: Apr. 3, 2023

(65) Prior Publication Data

US 2023/0346571 A1    Nov. 2, 2023

Related U.S. Application Data

(60) Provisional application No. 63/327,510, filed on Apr. 5, 2022.

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/446* (2013.01); *A61F 2/4611* (2013.01);
(Continued)

(58) Field of Classification Search
None
See application file for complete search history.

(56) References Cited

U.S. PATENT DOCUMENTS

| 3,117,459 A | 1/1964 | Schweitzer et al. |
| 5,651,745 A | 7/1997 | Childress |

(Continued)

FOREIGN PATENT DOCUMENTS

| CN | 102824234 A | 12/2012 |
| WO | 2009064787 A2 | 5/2009 |
| WO | 2021-231308 A1 | 11/2021 |

OTHER PUBLICATIONS

International Search Report, International Patent Application No. PCT/US2023/017305, Jul. 25, 2023, 3 pages.
(Continued)

*Primary Examiner* — Tessa M Matthews
(74) *Attorney, Agent, or Firm* — Hoffmann & Baron, LLP

(57) ABSTRACT

An expandable spinal implant comprises a body having a hollow interior, a proximal end and a distal end, the body supporting an endplate movable relative to the body in a first direction away from said body. An actuatable expansion mechanism, supported within the hollow interior is coupled to the body and the movable endplate to move the movable endplate relative to the body. The expansion mechanism comprises a rotatable drive gear and a rotatable follower supported spaced from the drive gear, and a transmission belt rotatively coupling the drive gear and the follower to transfer rotative motion from the drive gear to the follower upon actuation of the expansion mechanism. The transmission belt is formed in a continuous loop extending in an oblong shape around the drive gear and the follower and has an inward curve on one side of the loop between said drive gear and the follower.

21 Claims, 19 Drawing Sheets

(52) U.S. Cl.
CPC .............. *A61F 2002/30405* (2013.01); *A61F 2002/30523* (2013.01); *A61F 2002/30556* (2013.01); *A61F 2002/30579* (2013.01); *A61F 2002/4627* (2013.01)

(56) References Cited

U.S. PATENT DOCUMENTS

| | | |
|---|---|---|
| 5,800,300 A | 9/1998 | Childress |
| 6,190,414 B1 | 2/2001 | Young et al. |
| 6,454,806 B1 | 9/2002 | Cohen et al. |
| 6,692,495 B1 | 2/2004 | Zacouto |
| 6,752,832 B2 | 6/2004 | Neumann |
| 6,953,477 B2 | 10/2005 | Berry |
| 6,974,480 B2 | 12/2005 | Messerli et al. |
| 7,575,580 B2 | 8/2009 | Lim et al. |
| 7,588,573 B2 | 9/2009 | Berry |
| 7,691,147 B2 | 4/2010 | Gütlin et al. |
| 7,708,779 B2 | 5/2010 | Edie et al. |
| 7,806,932 B2 | 10/2010 | Webb et al. |
| 7,854,766 B2 | 12/2010 | Moskowitz et al. |
| 7,892,239 B2 | 2/2011 | Warnick et al. |
| 7,967,867 B2 | 6/2011 | Barreiro et al. |
| 7,976,549 B2 | 7/2011 | Dye et al. |
| 8,043,293 B2 | 10/2011 | Warnick |
| 8,157,845 B2 | 4/2012 | Warnick et al. |
| 8,192,495 B2 | 6/2012 | Simpson et al. |
| 8,292,959 B2 | 10/2012 | Webb et al. |
| 8,303,663 B2 | 11/2012 | Jimenez et al. |
| 8,323,345 B2 | 12/2012 | Sledge |
| 8,353,963 B2 | 1/2013 | Glerum |
| 8,366,777 B2 | 2/2013 | Matthis et al. |
| 8,444,650 B2 | 5/2013 | Warnick et al. |
| 8,529,627 B2 | 9/2013 | Baynham |
| 8,636,746 B2 | 1/2014 | Jimenez et al. |
| 8,771,360 B2 | 7/2014 | Jimenez et al. |
| 9,078,767 B1 | 7/2015 | McLean |
| 9,345,586 B2 | 5/2016 | Hunt et al. |
| 9,358,125 B2 | 6/2016 | Jimenez et al. |
| 9,474,626 B2 | 10/2016 | Jimenez et al. |
| 9,492,283 B2 | 11/2016 | Glerum |
| 9,492,286 B2 | 11/2016 | Biedermann et al. |
| 9,532,883 B2 * | 1/2017 | McLuen ................ A61F 2/28 |
| 9,642,722 B2 | 5/2017 | Baynham |
| 9,782,265 B2 | 10/2017 | Weiman et al. |
| 9,956,088 B2 | 5/2018 | Glerum |
| 10,172,718 B2 * | 1/2019 | Wolters ................ A61F 2/442 |
| 10,226,358 B2 | 3/2019 | Glerum |
| 10,307,254 B2 | 6/2019 | Levy et al. |
| 10,327,919 B2 | 6/2019 | Hunt et al. |
| 10,369,008 B2 | 8/2019 | Jimenez et al. |
| 10,548,738 B2 | 2/2020 | Milz et al. |
| 10,842,640 B2 | 11/2020 | Weiman et al. |
| 11,052,547 B2 | 7/2021 | Okumura et al. |
| 11,337,825 B2 | 5/2022 | Predick et al. |
| 11,419,735 B2 | 8/2022 | Barreiro et al. |
| 11,534,311 B2 | 12/2022 | Emerick et al. |
| 2005/0027360 A1 | 2/2005 | Webb et al. |
| 2005/0096745 A1 | 5/2005 | Andre et al. |
| 2006/0136062 A1 | 6/2006 | DiNello et al. |
| 2006/0229627 A1 | 10/2006 | Hunt et al. |
| 2008/0065082 A1 | 3/2008 | Chang et al. |
| 2008/0140085 A1 | 6/2008 | Gately et al. |
| 2010/0286779 A1 | 11/2010 | Thibodeau |
| 2011/0130835 A1 | 6/2011 | Ashley et al. |
| 2014/0288652 A1 * | 9/2014 | Boehm ................ A61F 2/4611 623/17.15 |
| 2014/0316522 A1 * | 10/2014 | Weiman ................ A61F 2/4455 623/17.16 |
| 2018/0243107 A1 | 8/2018 | Foley et al. |
| 2018/0318102 A1 | 11/2018 | Seifert et al. |
| 2020/0405499 A1 | 12/2020 | Gerbec et al. |
| 2022/0265440 A1 | 8/2022 | Lauf et al. |

OTHER PUBLICATIONS

Written Opinion of the International Searching Authority, International Patent Application No. PCT/US2023/017305, Jul. 25, 2023, 5 pages.

\* cited by examiner

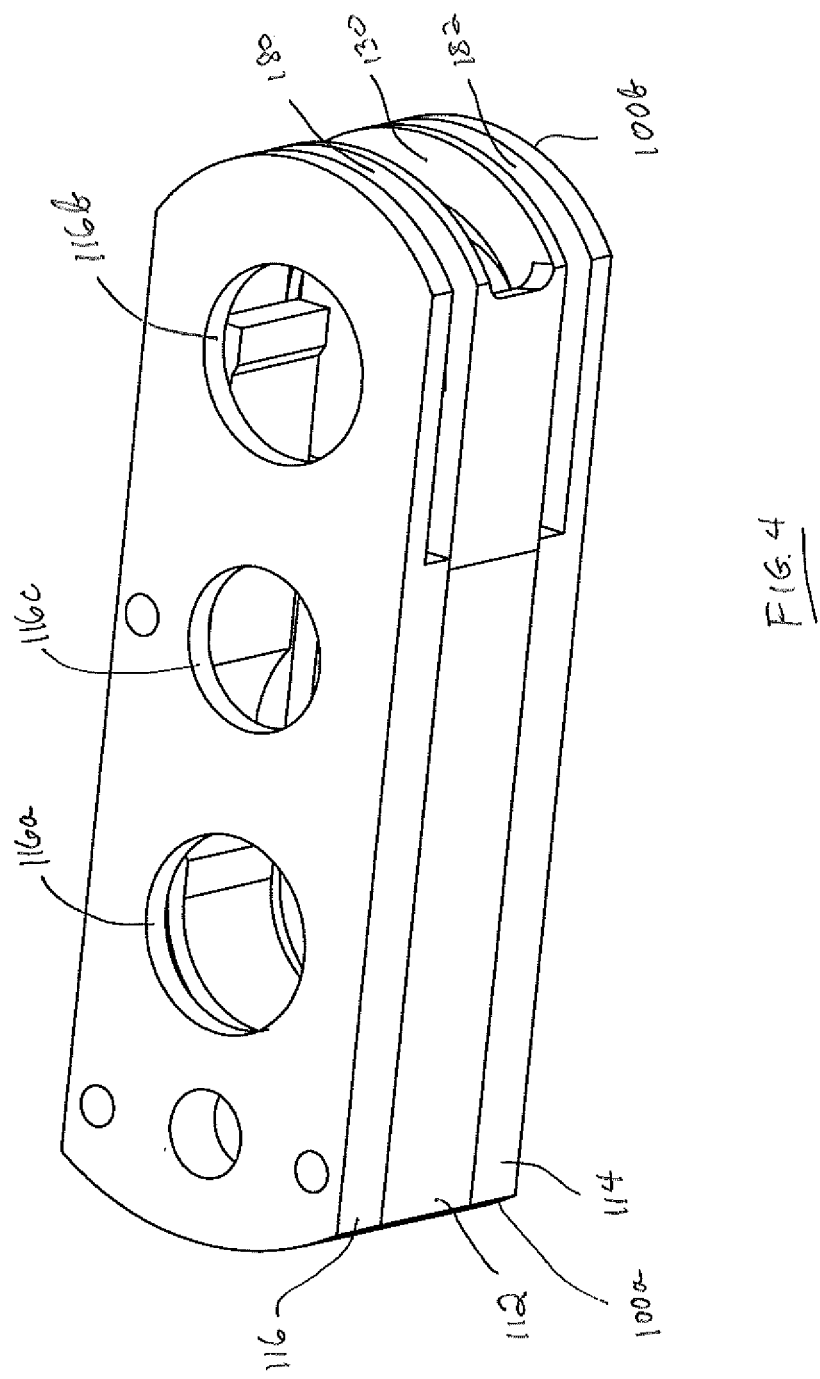

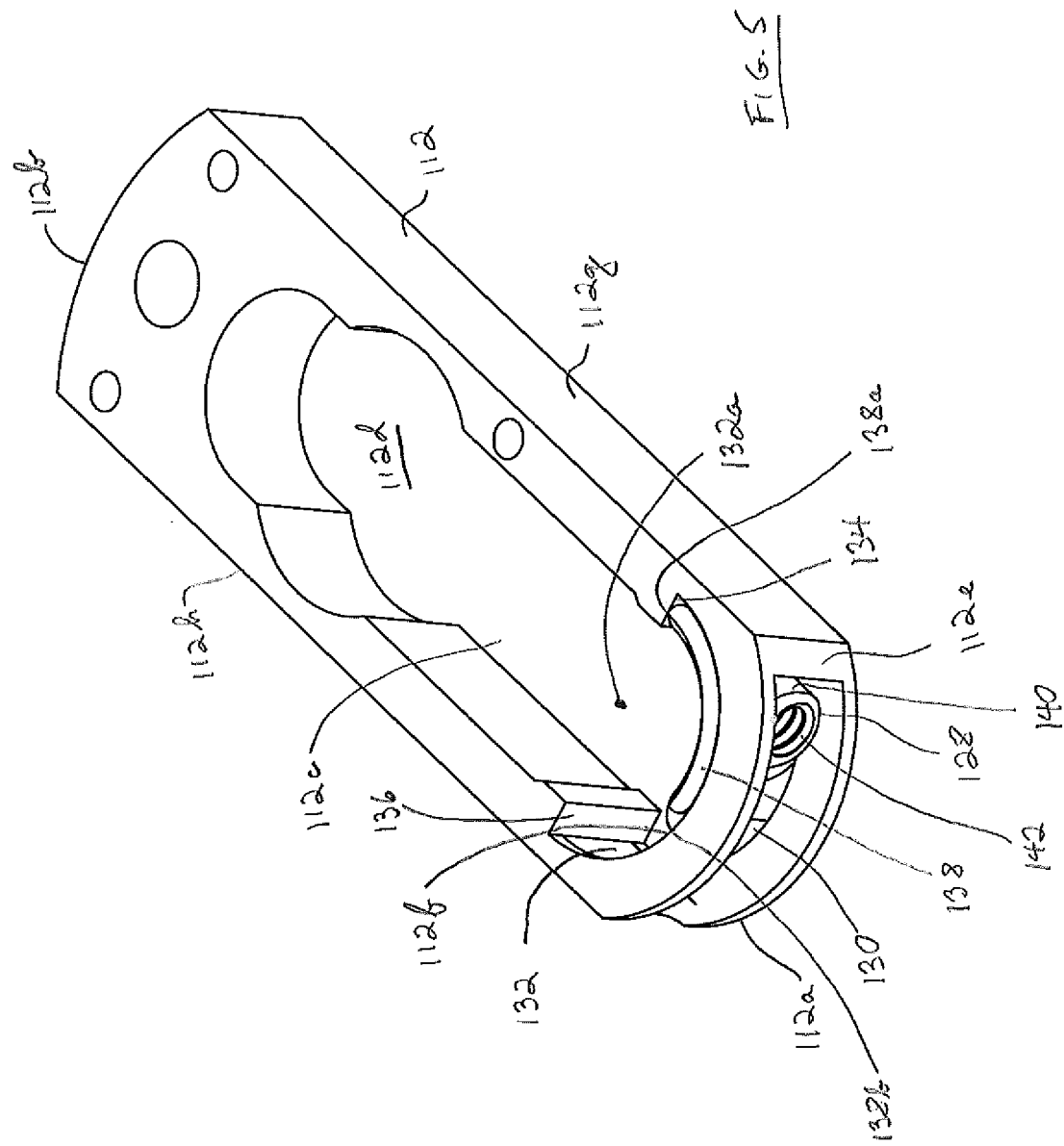

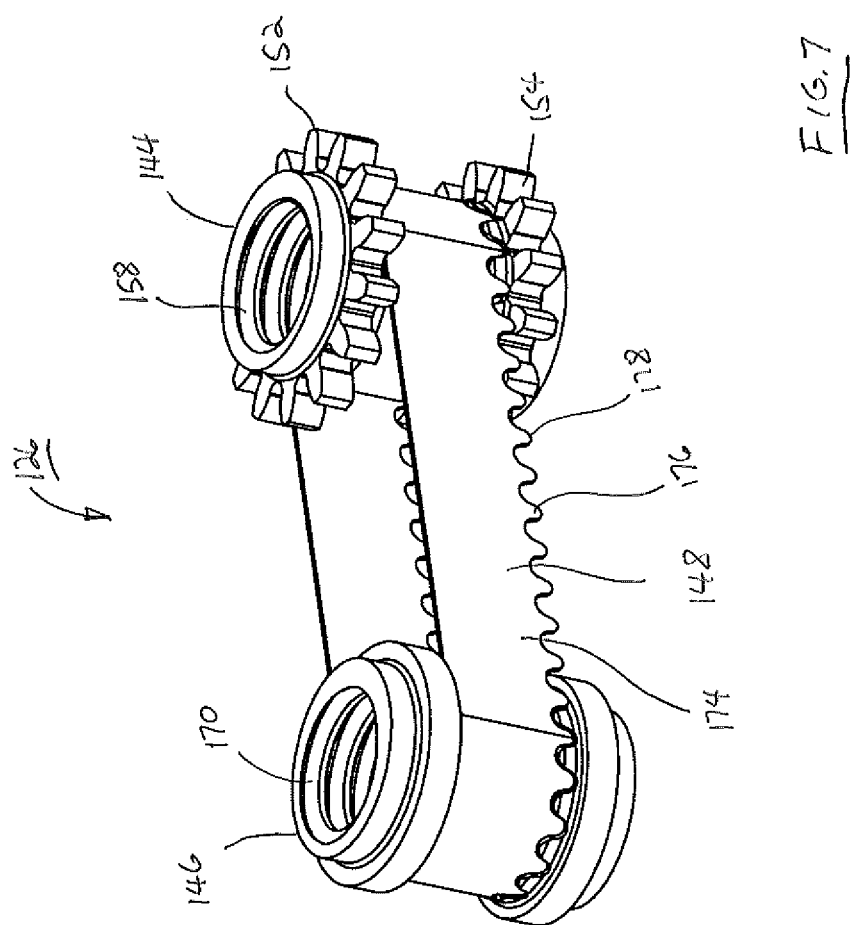

BELT DRIVEN EXPANDABLE INTERBODY FUSION DEVICE

CROSS-REFERENCE TO RELATED APPLICATION

This application claims the benefit of U.S. Provisional Patent Application No. 63/327,510, filed Apr. 5, 2022, the entire contents of which are incorporated by reference herein.

FIELD OF THE INVENTION

The subject invention relates generally to the field of spinal implants and more particularly to a transmission belt driven expandable interbody fusion device for insertion into the disc space of a patient and expanding the device in the disc space.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft, or bone substitute material is placed substantially in and/or adjacent the device in order to promote fusion between two adjacent vertebrae.

There are a variety of implants for spinal fusion in current use, some of which are expandable and others of fixed dimension. In order to accommodate the spinal anatomy and promote arthrodesis, an interbody fusion device preferably has optimized contact with adjacent endplates. This is commonly achieved by ensuring that the interface between the device and the bony endplates of opposing vertebral bodies includes a surface area as large as practicable. Expandable interbody fusion devices have been particularly used for this purpose. Exemplary expandable interbody fusion devices are described in U.S. Pat. No. 7,967,867, entitled "Expandable Interbody Fusion Device", which issued to Peter Barriero et al. on Jun. 28, 2011 (the '867 Patent) and U.S. Pat. No. 9,078,767, entitled "Expandable Spinal Interbody Fusion Device", which issued to Scott McLean on Jul. 14, 2015 (the '767 Patent). The '867 Patent and the '767 Patent are assigned to the same assignee as the present invention While these devices represent significant advances in the spinal fusion art, an improved expandable interbody fusion device that is capable of distracting opposed vertebral bodies in a spine under load is still desirable.

SUMMARY OF THE INVENTION

It is an object of the invention to provide an improved expandable spinal implant.

It is another object of the invention to provide an expandable spinal implant that includes a belt-driven expansion mechanism.

DESCRIPTION OF THE FIGURES

FIG. 4 is a top perspective view of assembled components of the subject steerable expandable interbody fusion device, namely the center body, upper plate and lower plate FIG. 5 is a top perspective view of the center body shown in FIG. 4 of the subject steerable expandable interbody fusion device illustrating a slidable brake at the proximal end thereof.

FIG. 7 is a perspective view of an expansion mechanism for increasing the height of the subject steerable expandable interbody fusion device, showing a drive gear, a spindle and a power transmission band coupling the drive gear and spindle.

DESCRIPTION OF THE EMBODIMENTS

Figure 1:
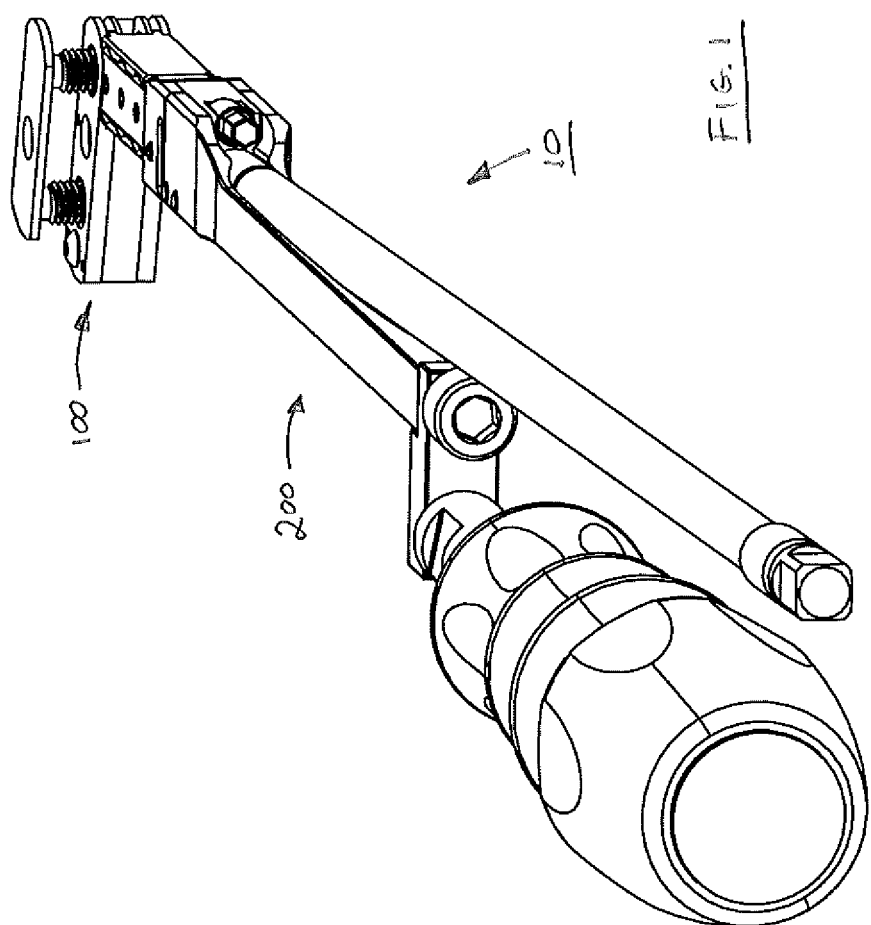
FIG. 1 is a top perspective view of an apparatus for use in spinal interbody fusion surgery according to a first embodiment of the invention comprising a steerable expandable interbody fusion device attached to an associated inserter with the subject steerable expandable interbody fusion device being in an expanded condition and having been rotated relative to the subject inserter.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, there is shown an apparatus 10 according to a first embodiment for use in spinal interbody fusion surgery comprising a steerable expandable interbody fusion device 100, attached to an associated inserter 200. Inserter 200 is configured to releasably attach to device 100 and to facilitate insertion of device 100 into an intervertebral disc space. Once placed within the disc space, device 100 may be pivotably rotated to a desired location in the disc space and expanded therein by actuation of inserter 200, as will be described. As shown in FIG. 1, device 100 is in the expanded condition having been pivoted relative to inserter 200 to a position chosen by the surgeon user.

In accordance with a particular exemplary arrangement, device 100 and instrument 200 are sized and configured for introducing device 100 in a posterolateral approach in a minimally invasive transforaminal lumbar interbody fusion (TLIF) procedure. It should be appreciated that while device 100 is particularly configured for use as a TLIF device, it, may also be used as an expandable interbody fusion device that may be introduced in other approaches, such as in the posterior direction at different levels of the spine, in the oblique anterior/lateral direction (OLIF), or in open surgical procedures.

Figure 2:
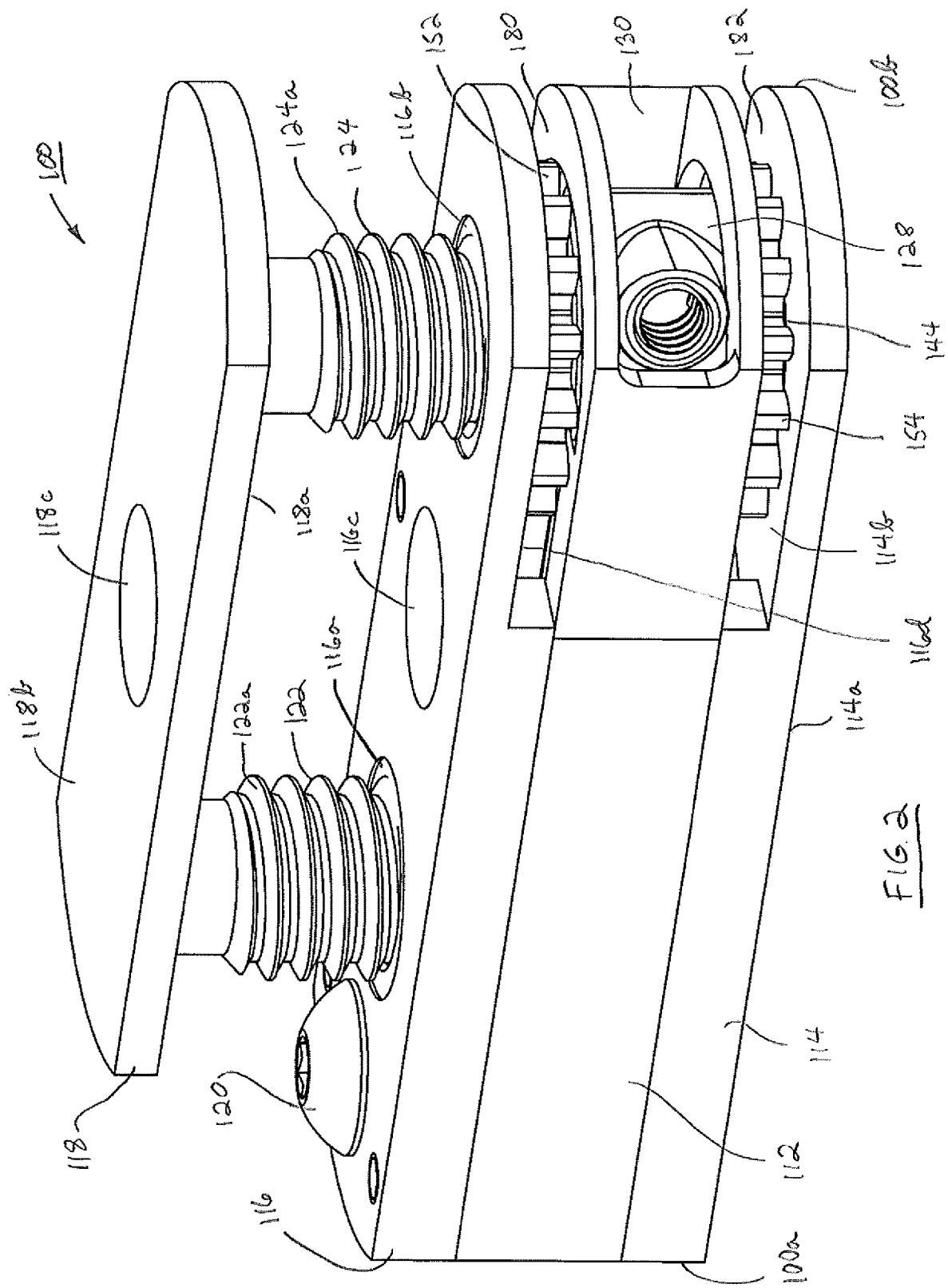
FIG. 2 is a perspective view of the subject steerable expandable interbody fusion device shown in the expanded condition of FIG. 1.
Figure 3:
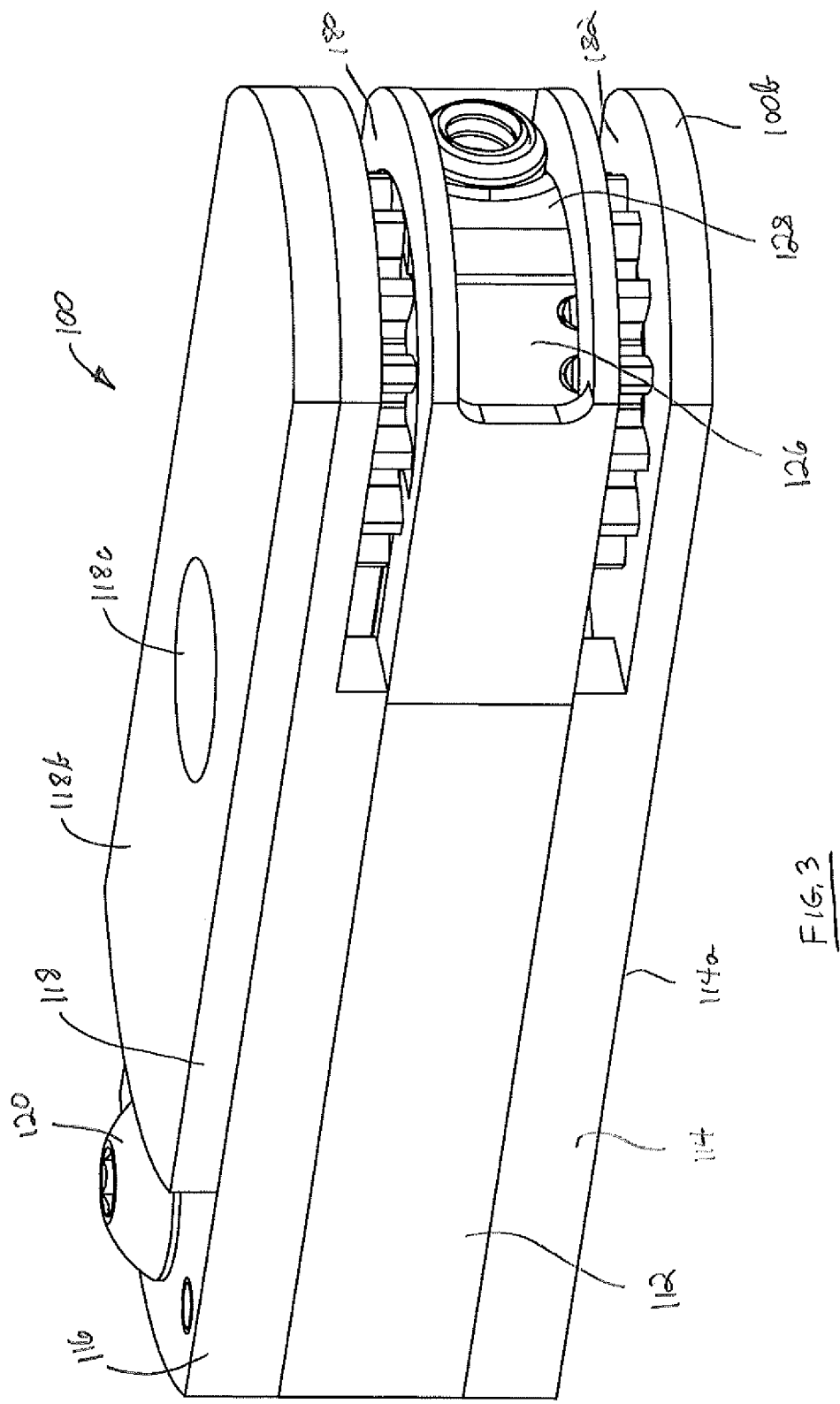
FIG. 3 is a perspective view of the subject steerable expandable interbody fusion device of FIG. 2 shown in an unexpanded condition and prior to having been rotated.

Turning now to FIGS. 2, 3 and 4 details of steerable expandable interbody fusion device 100 are described. Device 100 comprises a hollow center body 112, a lower plate 114, an upper plate 116 and a movable endplate 118 that upon movement expands the height of device 100. Upper plate 116, center body 112 and lower plate 114 may be fixedly joined by a suitable fastener, such as a screw 120. While the present exemplary arrangement includes a fastener screw 120, it should be appreciated that upper plate 116, center body 112 and lower plate 114 may also be welded to provide surfaces free of protrusions, which would more desirably present no obstructions to intervertebral placement of device 100. Movement of movable endplate 118 is effected by threaded telescoping posts 122 and 124 that are each respectively fixedly attached to a bottom surface 118a of movable endplate 118. Threaded post 122 is located adjacent to a distal end 100a of device 100 and threaded post 124 is located adjacent to a proximal end 100b of device 100. Threaded posts 122 and 124 respectively extend through openings 116a and 116b of upper plate 116 into an expansion mechanism 126 supported on lower plate 114 and within center body 112. Actuation of expansion mechanism 126 causes telescoping movement of threaded posts 122 and 124, as will be explained. Device 100 includes at proximal end 100b a brake 128 that is supported by center body 112 for arcuate movement relative to center body 112, the purpose and function of which will be described.

Movable endplate 118 includes a top surface 118b configured for contact with an endplate of a first vertebral body that communicates with the disc space to be treated. Similarly, lower plate 114 includes a bottom surface 114a configured for contact with an endplate of a second opposing vertebral body that communicates with the disc space to be treated. Top surface 118b and bottom surface 114a may each be suitably roughened to have a textured surface to facilitate microintegration of device 100 with the respective vertebral bodies to promote fusion with device 100. Such surface texturing may be formed by a laser ablation process as more fully described in commonly owned U.S. patent application Ser. No. 17/547,640, entitled "Expandable TLIF Device and Related Insertion and Grafting Instrumentation", filed by Peter Barriero et al. on Dec. 10, 2021 (the '640 Application), now U.S. Pat. No. 11,419,735, which issued on Aug. 23, 2022, the entire contents of which are incorporated by reference herein. It should be understood that other suitable surface roughening techniques, such as acid etching may also be used. Upper plate 116 and movable endplate 118 may have openings 116c and 118c, respectively formed therethrough in communication with hollow center body 112 to facilitate fusion of bone graft within device 100 to the first vertebral body. Lower plate 114 may also have a similar opening (not shown) therethrough to facilitate fusion of bone graft with the second opposing vertebral body.

Figure 6B:
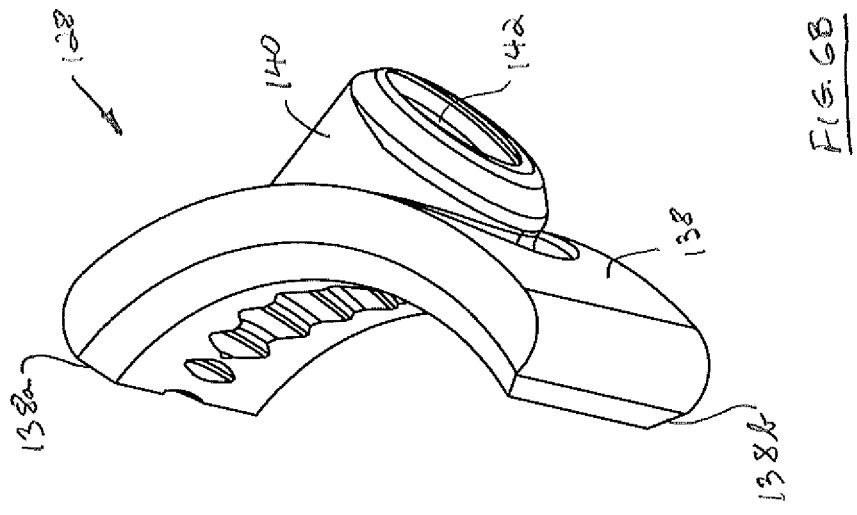
FIG. 6B is a top perspective view of the brake shown in FIG. 6A.
Figure 6A:
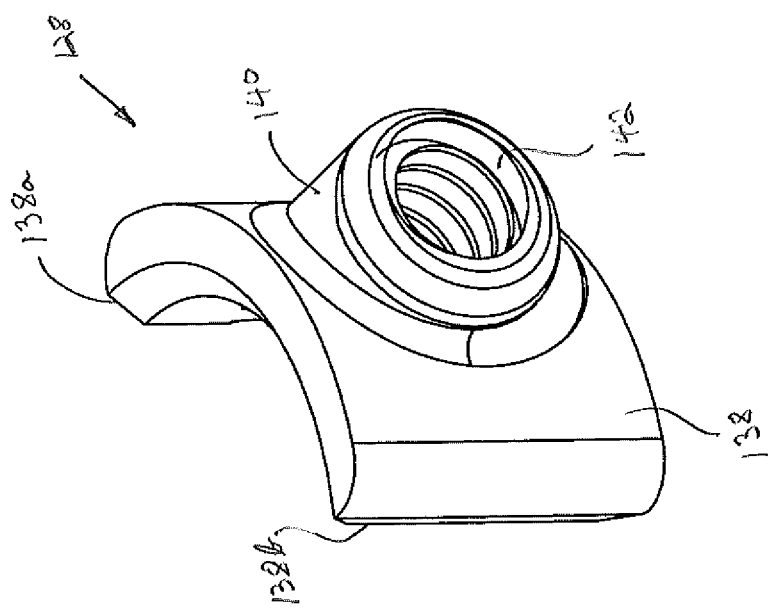
FIG. 6A is a front perspective view of the brake shown in FIG. 5.

Turning now also to FIGS. 5 and 6A and 6B, details of the device center body 112 and brake 128 are described. As illustrated in FIG. 5, center body 112 has a proximal end 112a, a distal end 112b and an opening 112c extending therethrough to define a hollow interior 112d of center body 112. Center body 112 includes an arcuate front wall 112e having an access window 130 extending therethrough in communication with hollow interior 112d. Front wall 112e has an interior arcuate surface 112f defining a curved path 132 within which brake 128 is configured to move, as will be described. The arcuate extent of curved path 132 is defined by a first stop surface 134 adjacent one side 112g of center body 112 and a second stop surface 136 adjacent the opposite side 112h of center body 112, as depicted in FIG. 5. In a particular arrangement, curved path 132 traverses an arcuate extent of approximately 180°, although an arcuate extent of less than 180° may be considered. Curved path 132 is configured to have a radius of curvature having a center point 132a located in hollow interior 112d, as shown in FIG. 5. Center point 132a is configured to axially coincide with the axis of the drive gear of expansion mechanism 126, as will be described.

Referring now to FIGS. 6A and 6B, further details of brake 128 are described. Brake 128 comprises a curved brake shoe 138 and a boss 140 projecting angularly therefrom. Brake shoe 138 includes a first end 138a and an opposite second end 138b. The radius of curvature of curved brake shoe 138 is substantially the same as the radius of curvature of curved path 132 as described above. As such, brake shoe 138 is configured to slide within curved path 132 of center body 112. The arcuate extent of brake shoe 138 is defined by the arcuate distance between first end 138a and second end 138b. To allow articulating travel of brake shoe 138 within curved path 132, the arcuate extent of brake shoe 138 is less than the arcuate extent of curved path 132. For example, to allow brake shoe 138 to arcuately travel approximately 80° in a curved path 132 of 180°, the arcuate extent of brake shoe 138 would be approximately 100°. Depending upon the extent brake shoe 138 is desired to arcuately travel, the dimensions of the arcuate extents of curved path 132 and brake shoe 138 may be varied such that brake shoe 138 may travel more or less than 80°. Boss 140 has a generally cylindrical configuration and is sized to extend for access into window 130 and to move therewithin with the arcuate movement of brake shoe 138. Boss 140 includes interior threads 142 for threadable connection to an attachment shaft rotatably supported by inserter 200, as will be described. In the position shown in FIG. 5, the first end 138a of brake shoe 138 is in contact with first stop surface 134. When brake 128 is held in a fixed position by inserter 200, center body 112 and hence device 100 may rotatably pivot in a first direction about center point 132a on brake shoe 138 until second end 138b of brake shoe 138 comes into contact with second stop surface 136. In this position, device 100 will be constrained from any further rotation in the first direction. In an alternative arrangement, the arcuate distance that brake shoe 138 travels within curved path 132 for constraint purposes may also be controlled by the size of boss 140 and the arcuate extent of access window 130.

Figure 8A:
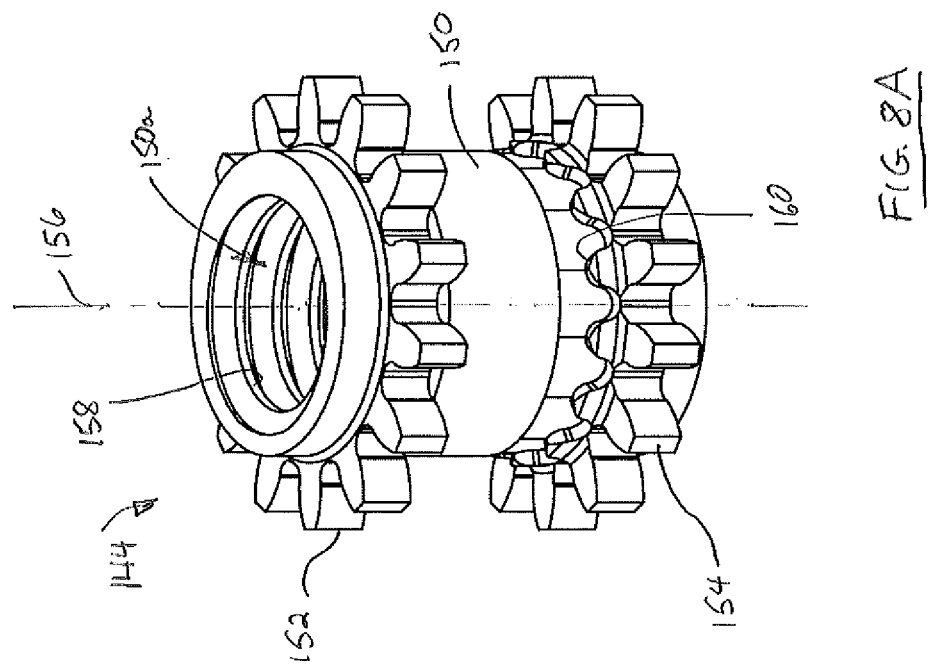
FIG. 8A is a top perspective view of the drive gear of the expansion mechanism shown in FIG. 7.
Figure 8B:
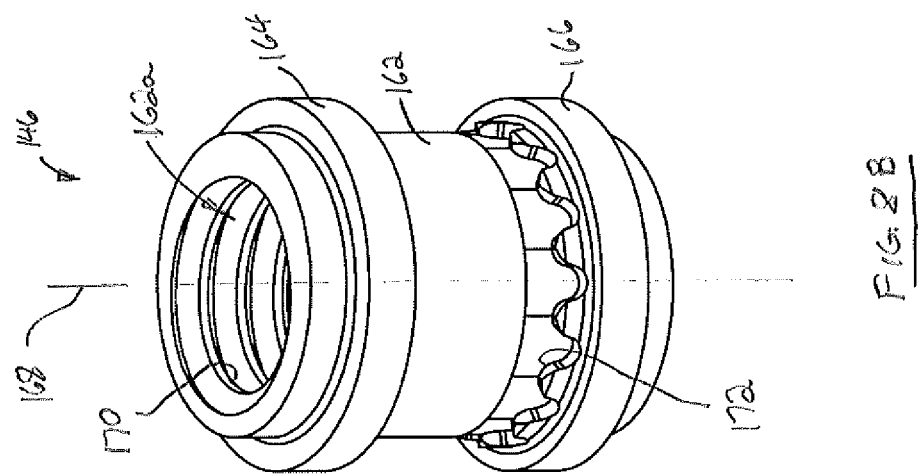
FIG. 8B is a top perspective view of the spindle of the expansion mechanism shown in FIG. 7.
Figure 9:
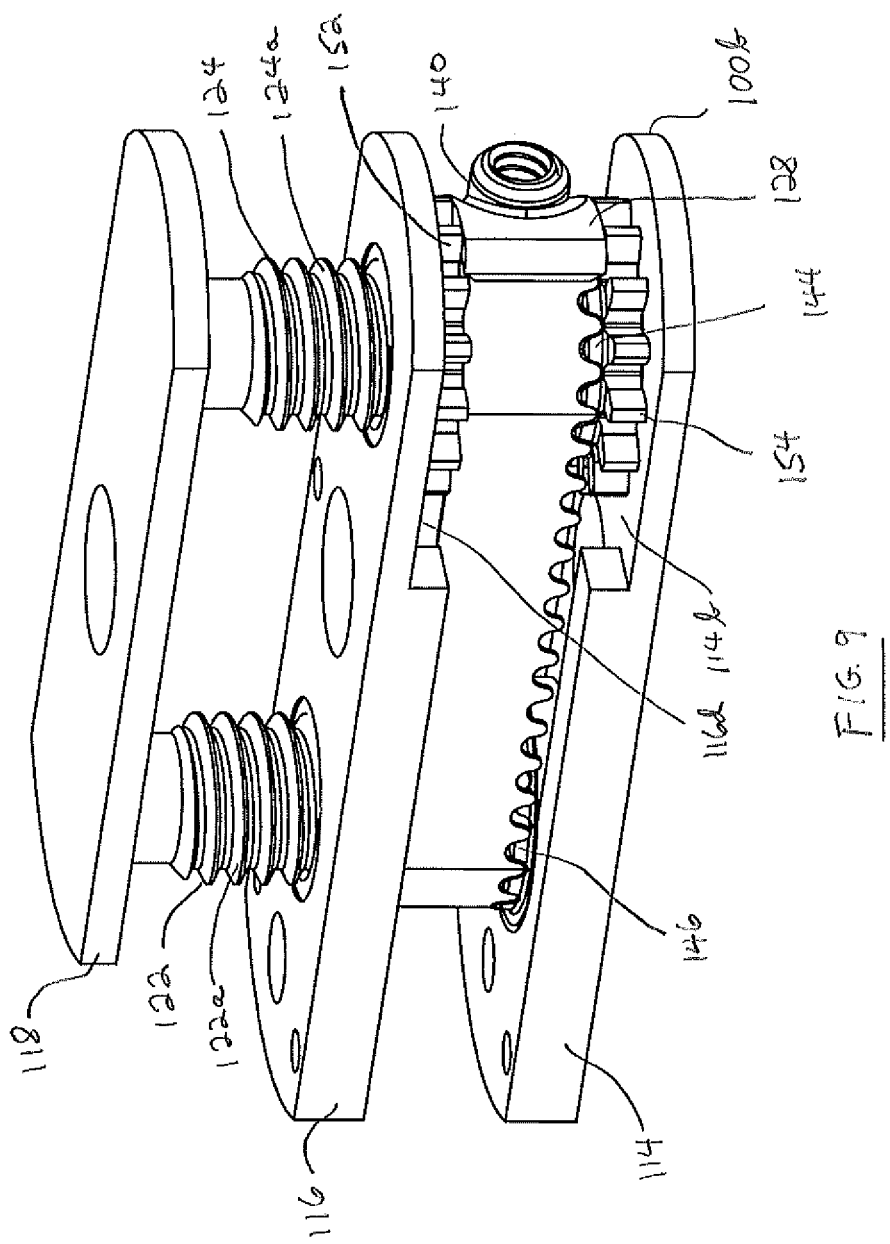
FIG. 9 is a modified view of the subject steerable expandable interbody fusion device of FIG. 2 with center body removed to reveal details of the expansion mechanism.

Turning now to FIGS. 7, 8A, 8B and 9, details of expansion mechanism 126 are described. Expansion mechanism 126 comprises as illustrated in FIG. 7 a drive gear 144, a spindle 146, which serves as a follower of drive gear 144, and a power transmission band 148 that couples drive gear 144 and spindle 146. Power transmission band 148 transfers rotative motion from drive gear 144 to spindle 146, as will be described. Referring particularly to FIG. 8A, drive gear 144 comprises a generally cylindrical central hub 150 supporting an upper level of gear teeth 152 and a lower level of gear teeth 154. Gear teeth 152 and 154 project radially outwardly from and are axially spaced from each other. Geer teeth 152 and 154 are configured on central hub 150 to mesh with gears of inserter 200, as will be described. As shown in FIG. 9, drive gear 144 is supported on lower plate 114 at the proximal end 100b of device 100 for rotation thereon about a central axis 156 (see FIG. 8A). Lower level of gear teeth 154 resides in a recess 114b formed at the proximal end of lower plate 114. Upper level of gear teeth 152 resides in a recess 116d formed at the proximal end of upper plate 116. As noted above, axis 156 about which drive gear 144 rotates, coincides with center point 132a about which brake shoe 138 rotates in curved path 132 of center body 112. Central hub 150 has a central opening 150a that includes interior threads 158 to threadably interengage with exterior threads 124a of threaded post 124 that is fixedly attached to movable endplate 118. Disposed adjacent the lower level of gear teeth 154 is a set of motion transfer teeth 160 that extend circumferentially around and project axially along central hub 150. Motion transfer teeth 160 are configured to mesh with teeth on power transmission band 148, as will be described.

Referring now to FIG. 8B, spindle 146 comprises a generally cylindrical central hub 162 including an upper flange 164 and a lower flange 166 that are axially spaced from each other. Central hub 162 has a diameter approximately the same as the diameter of central hub 150 of drive gear 144. As shown in FIG. 9, spindle 146 is supported on lower plate 114 at the distal end 100a of device 100 for rotation thereon about its central axis 168. Central hub 162 has a central opening 162a that includes interior threads 170 to threadably interengage with exterior threads 122a of threaded post 122 that is fixedly attached to movable endplate 118. Disposed adjacent lower flange 166 is a set of motion transfer teeth 172 that extend circumferentially around and project axially along central hub 162. Motion transfer teeth 160 are configured to mesh with teeth on power transmission band 148. The pitch of motion transfer teeth 172 of spindle 146 is substantially the same as the pitch of motion transfer teeth 160 of drive gear 144.

Referring again to FIG. 7, power transmission band 148 is formed of a continuous belt 174 of metal. In a particular exemplary arrangement, belt 174 is comprised of nitinol, although other suitable biocompatible materials having sufficient elastic properties and strength characteristics may be used. A plurality of belt teeth 176 are formed along the entire lower edge 178 of belt 174. Belt teeth 176 are spaced at a distance substantially equal to the pitch of both motion transfer teeth 160 of drive gear 144 and motion transfer teeth 172 of spindle 146 such that belt teeth 176 interengage with motion transfer teeth 160 and motion transfer teeth 172. Accordingly, upon rotational movement of drive gear 144 by inserter 200, as will be described, motion is transferred from drive gear 144 through belt 174 to spindle 146 therefore causing rotation of spindle 146 at approximately the same rate as the rotation of drive gear 144. It should be understood that instead of belt teeth 176, appropriate holes may be formed through belt 174 to receive complementary teeth on central hubs 150 and 162 when formed as sprockets. Band 148 may also be formed as a timing belt to engage suitable complementary teeth formed on central hubs 150 and 162. Further variations for motion transfer may include posts that project radially outwardly from drive gear 144 and follower spindle 146 that are configured to extend into corresponding spaced holes extending along and through the center of belt 174. Additionally, longitudinal recesses may be formed into drive gear 144 and follower spindle 146 that are configured to receive longitudinally spaced teeth projecting inwardly along the length of belt 174 in a manner of a timing belt.

Referring back to FIG. 2, in the assembled configuration of device 100, gear teeth 152 at the upper level of drive gear 144 are exposed at distal end 100b of device 100 in an upper space 180 defined by upper plate recess 116d and the center body 112. Similarly, gear teeth 154 at the lower level of drive gear 144 are exposed at distal end 100b of device 100 in a lower space 182 defined by lower plate recess 114b and center body 112. As such, upper gear teeth 152 and lower gear teeth 154 are accessible to mesh with gears of inserter 200.

When rotational movement of device 100 relative to inserter 200 is not constrained by brake 128, rotation of drive gear 144 in the first direction will in a first mode of operation simultaneously rotate device 100 on brake 128 relative to inserter 200 about center point 132a. When rotational movement of device 100 relative to inserter 200 is constrained by brake 128 rotation of drive gear 144 in an opposite second direction will in a second mode of operation actuate expansion mechanism 126 causing rotation of spindle 146 and movement of movable endplate 118 upwardly away from upper plate 116 to thereby increase the height of device 100. When threaded posts 122 and 124 have approximately the same diameter and approximately the same pitch of threads 122a and 124a, rotation of drive gear 144 and spindle 146 at approximately the same rate will cause threaded posts 122 and 124 to telescopically advance along respective axes 156 and 168 to lift movable endplate 118 substantially parallel to upper plate 116 during such movement. It should be appreciated that rotatably attaching threaded posts 122 and 124 to movable endplate 118 and forming threaded posts 122 and 124 to have different diameters or pitch of threads 122a and 124a would result in non-parallel movement of movable endplate 118 away from upper plate 116. A similar effect may be provided by forming different diameters of drive gear central hub 150 and spindle central hub 162 to thereby cause a different rate of rotation between drive gear 144 and spindle 146. Such non-parallel movement of movable endplate 118 may be useful to correct lordosis prior to pivotal movement of device 100 in the disc space, and to correct coronal deformity after such pivotal movement of device 100.

Figure 10:
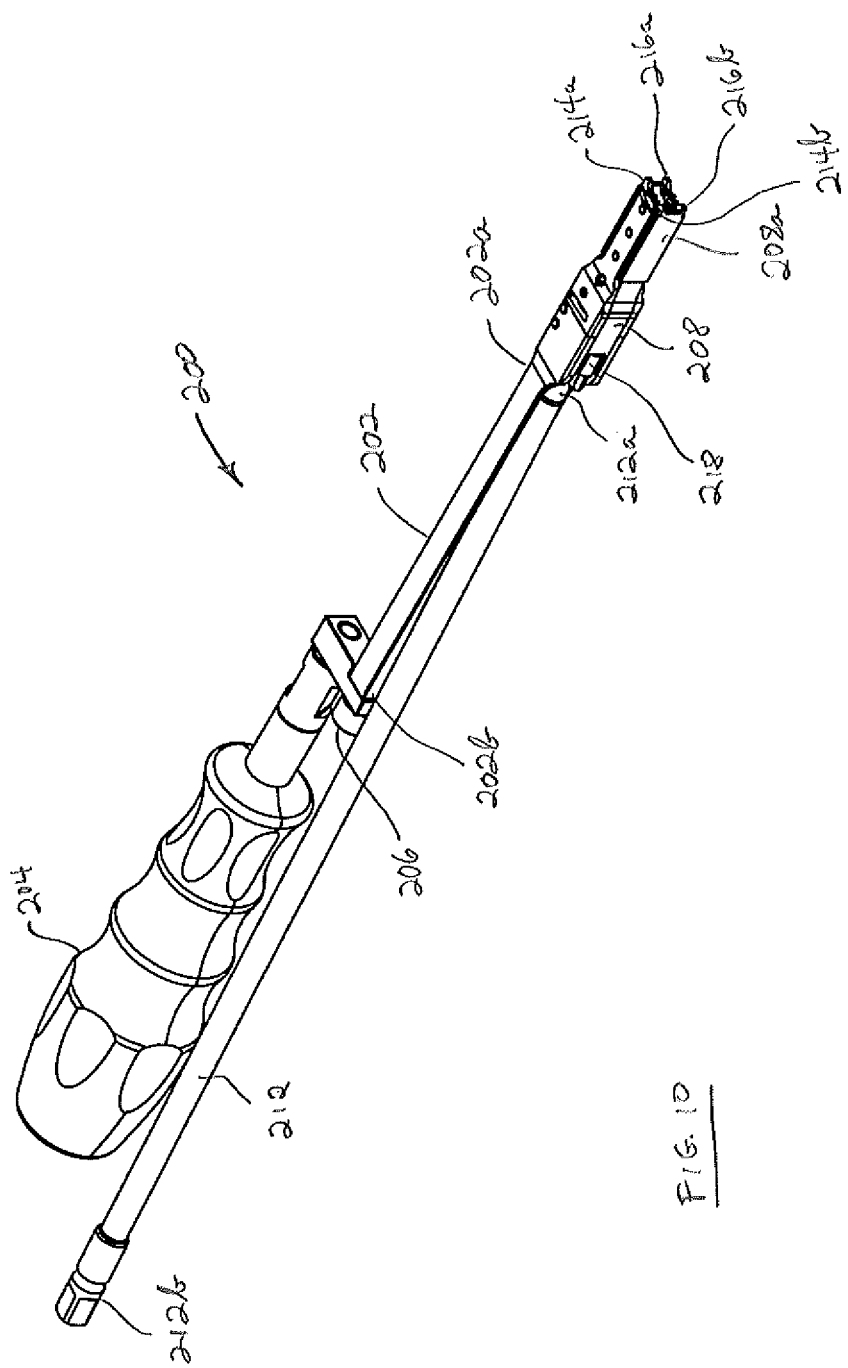
FIG. 10 is a top perspective view of the inserter of FIG. 1.
Figure 11:
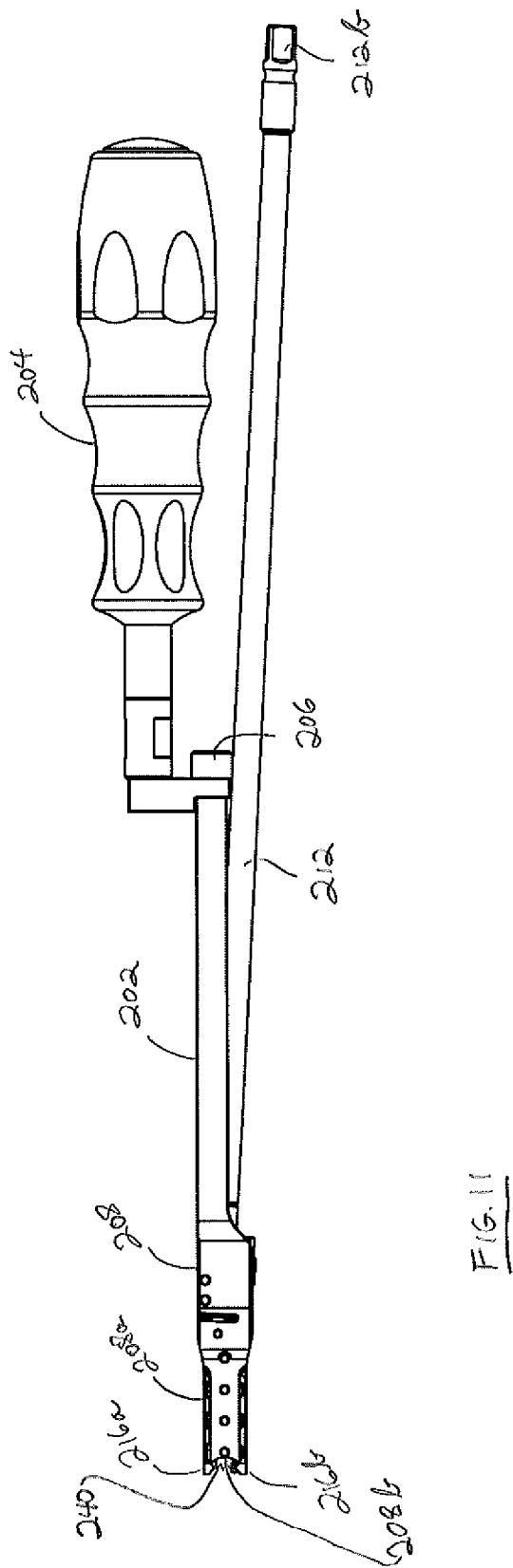
FIG. 11 a bottom plan view of the inserter of FIG. 10.

Turning now to FIGS. 10 through 14, further details of inserter 200 are described. As shown in FIGS. 10-11, inserter 200 comprises an elongate hollow tubular body 202 having a distal end 202a and a proximal end 202b. A handle 204 is suitably attached to proximal end 202b of tubular body 202. Handle 204 may be ergonomically configured for ease of manual grasping by a user and may be offset axially relative to tubular body 202. A fastener 206 is provided to removably attach handle 204 to tubular body 202. Inserter 200 includes at distal end 202a a housing 208 containing a drive mechanism 210 (see FIG. 12) for pivotally steering and expanding steerable expandable interbody fusion device 100. The distal end 208a of housing 208 is configured to have a generally rectangular shape that in a particular exemplary arrangement has a cross-sectional profile no greater than the cross-sectional profile of device 100 to which it is releasably attachable. Inserter 200 includes elongate drive shaft 212 that is removably coupled to drive mechanism 210 at its distal end 212a. The proximal end 212b may be configured to have a complementary shape, such as a square or hexagonal configuration, for detachable connection to a suitable tool to rotate drive shaft 212 in a manner to steer and expand device 100. The distalmost end of housing 208 includes a pair of upper stabilizing tabs 214a and 214b and lower stabilizing tabs 216a and 216b that are configured to respectively enter upper space 180 and lower space 182 of device 100 when inserter 200 is attached to device 100. Inserter 200 includes an attachment shaft 218 supported by housing 208 for attachment of inserter 200 to device 100.

Figure 12:
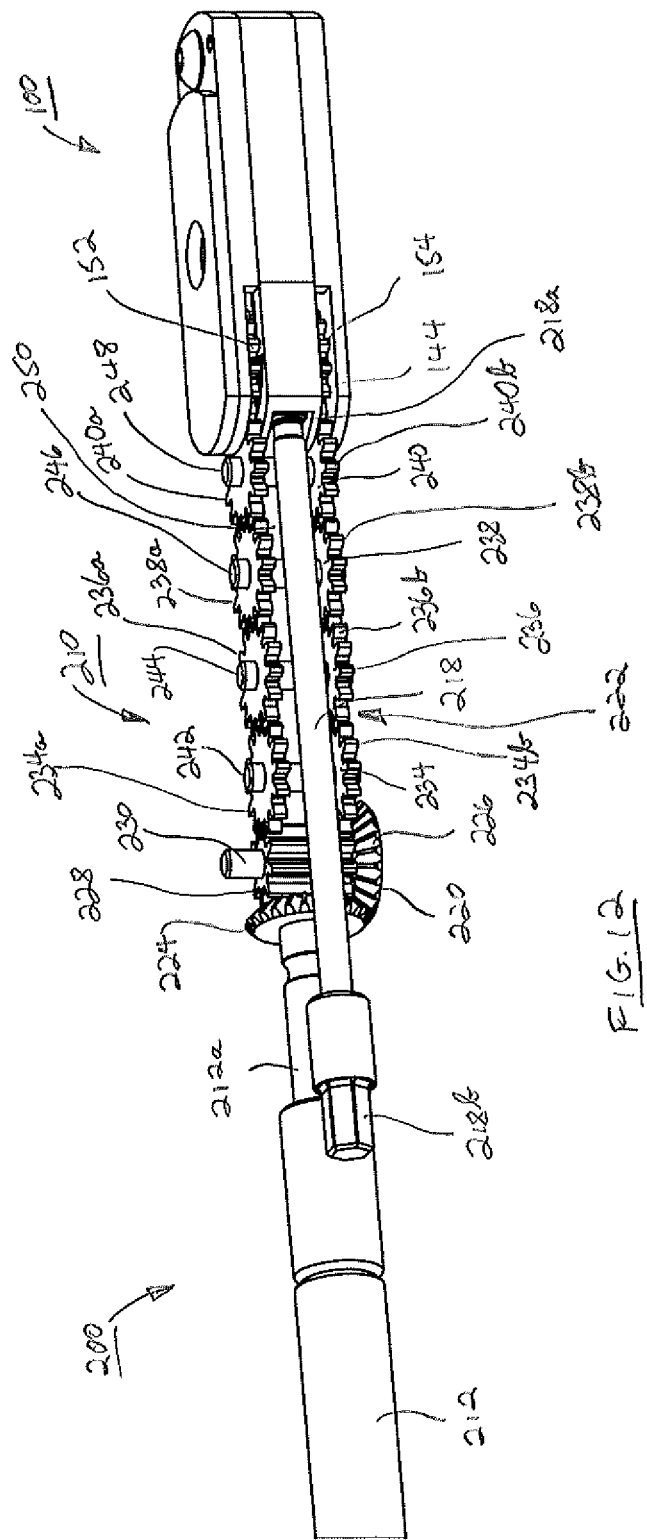
FIG. 12 is a perspective partial view of the distal end of the subject inserter shown attached to the subject steerable expandable interbody fusion device with the housing of the subject inserter removed to reveal the drive mechanism including a power drive and a gear train in a particular arrangement of the subject inserter.
Figure 13:
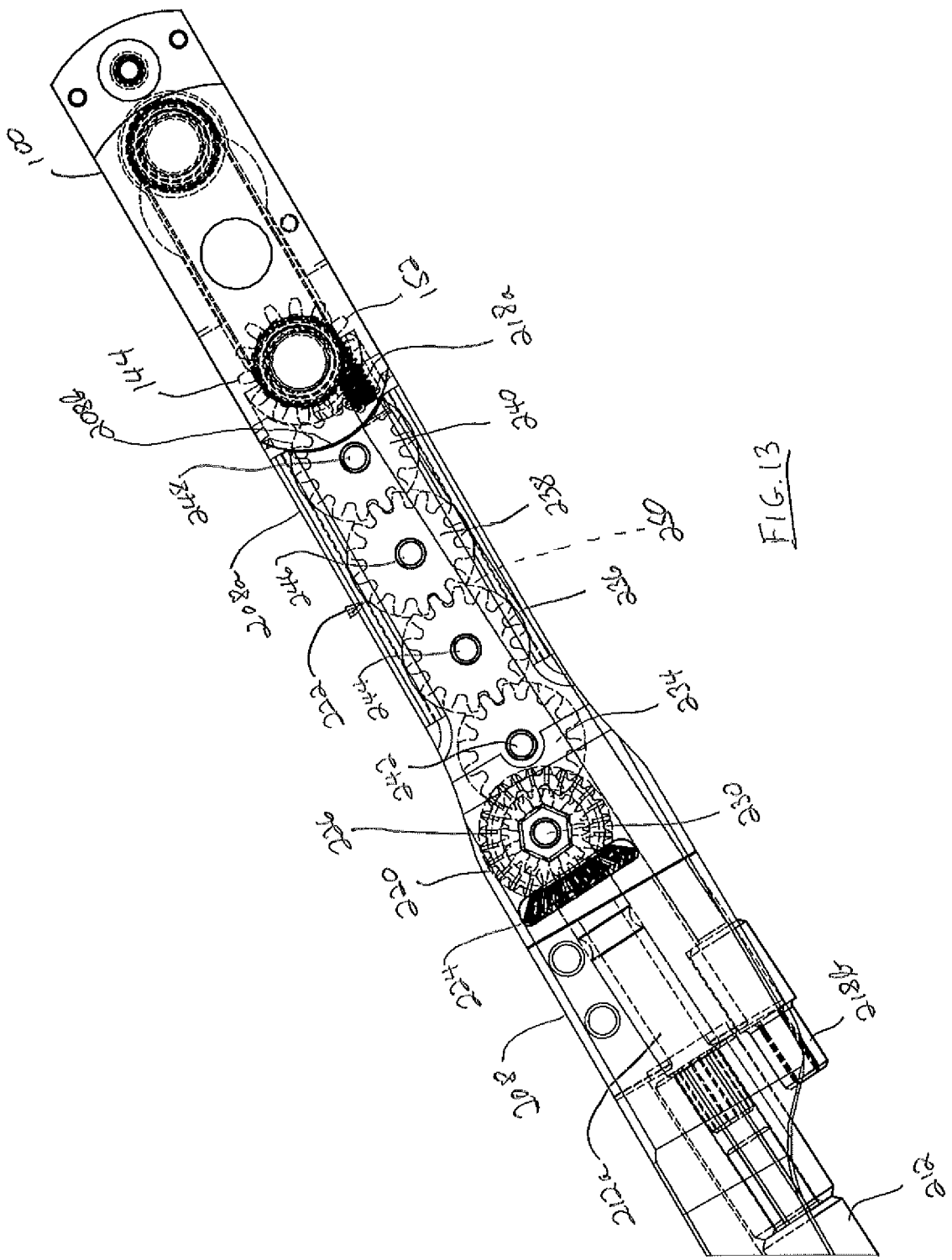
FIG. 13 is a top view of the distal end of the subject inserter shown attached to the subject steerable expandable interbody fusion device and showing in phantom the drive mechanism including the power drive and gear train in the particular arrangement of the subject inserter illustrated in FIG. 12.
Figure 14:
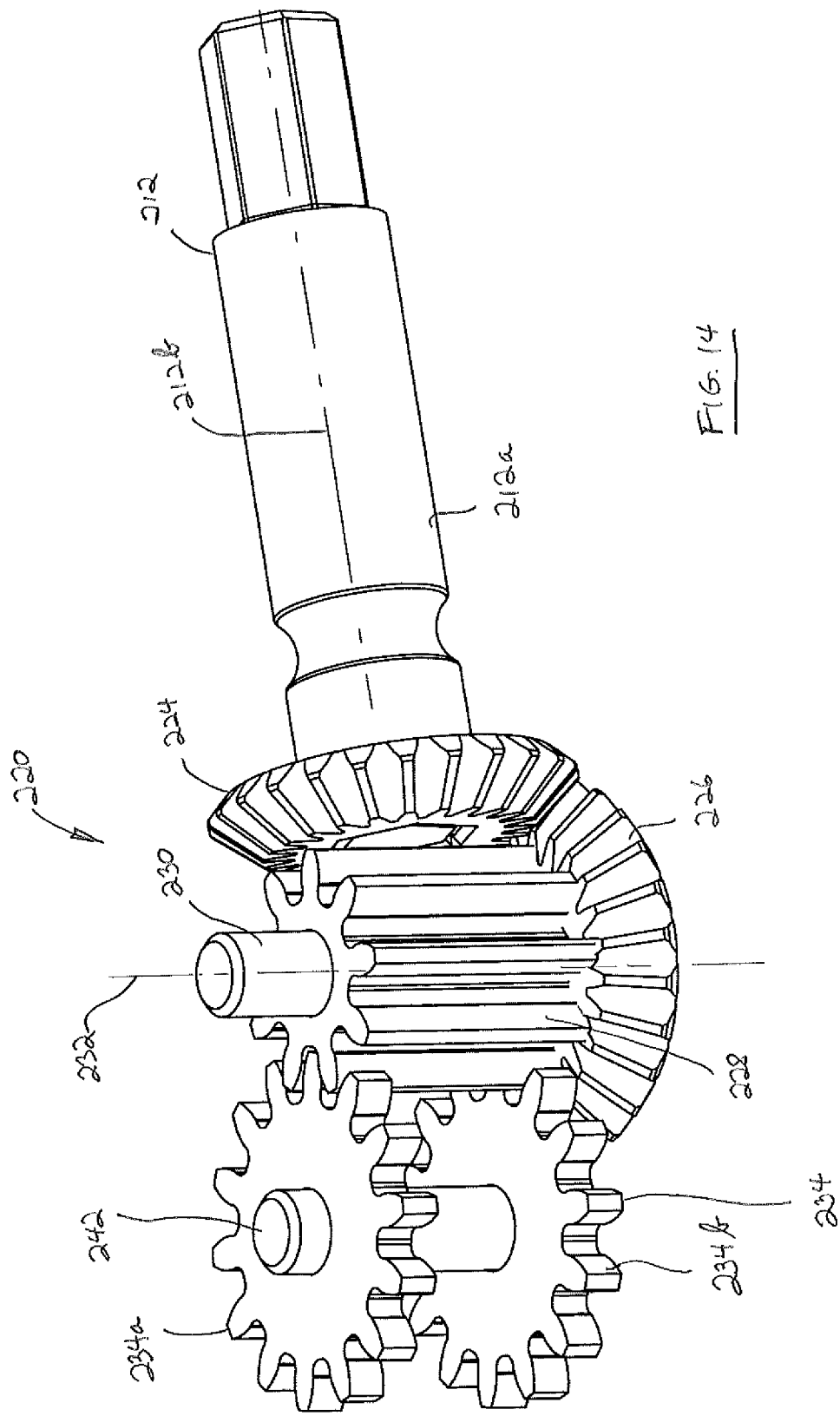
FIG. 14 is a top perspective view of the power drive of the drive mechanism of the subject inserter shown as meshing with the input gear of the gear train of FIG. 13.

Referring now to FIGS. 12, 13 and 14 details of drive mechanism 210 are described. Drive mechanism 210 comprises a power drive 220 and, in the particular exemplary arrangement shown, a gear train 222. Power drive 220 is suitably coupled in one axial direction of housing 208 to distal end 212a of drive shaft 212. Power drive 220 is coupled in an opposite axial direction to one axial end of gear train 222 and gear train 222 is coupled at an opposite axial end to drive gear 144 of device 100. As shown more particularly in FIG. 14, power drive 220 comprises a beveled driver gear 224, a beveled driven gear 226 and a spur gear 228. Spur gear 228 is fixed to beveled driven gear 226 for rotation therewith on an axle 230 that extends along an axis 232. Beveled driver gear 224 is fixedly coupled to drive shaft 212 for rotation therewith about an axis 212b that is substantially orthogonal to axis 232. As such, upon rotation of drive shaft 212 power is transferred from beveled driver gear 224 to beveled driven gear 226 causing rotation of both beveled driven gear 226 and attached spur gear 228. It should be understood that power drive 220 may alternatively be a worm gear or other suitable gear structure.

With reference again to FIGS. 12 and 13, gear train 222 in the particular exemplary configuration shown comprises four intermeshed gears that are disposed in a linear arrangement within housing distal end 208a. These four gears comprise an input gear 234, a first idler gear 236, a second of idler gear 238 and an output gear 240. Input gear 234 is rotatable on an axle 242 and includes an upper level of gears 234a and a lower level of gears 234b that are spaced along axle 242. Spur gear 228 of power drive 220 is of height to mesh with both the upper and lower levels of gears 234a and 234b of input gear 234. First idler gear 236 which meshes with input gear 234 is rotatable on an axle 244 and includes an upper level of gears 236a and a lower level of gears 236b that are spaced along axle 244. Second idler gear 238 which meshes with first idler gear 236 is rotatable on an axle 246 and includes an upper level of gears 238a and a lower level of gears 238b that are spaced along axle 246. Output gear 240 which meshes with second idler gear 238 is rotatable on an axle 248 and includes an upper level of gears 240a and a lower level of gears 240b that are spaced along axle 248. When inserter 200 is attached to device 100, the upper level of gears 240a and the lower level of gears 240b of output gear 240 are configured to respectively mesh with the upper level of gears 152 and the lower level of gears 154 of drive gear 144 of device 100. Each of axles 242, 244, 246 and 248 are substantially parallel to each other and to axle 230 of power drive 220. The upper and lower levels of drive gear 144 and input gear 234, first idler gear 236, second of idler gear 238, output gear 240 are provided so that upon rotation of inserter drive shaft 112 sufficient torque can be transferred from inserter 200 to device 100 to rotate and then expand device 100 within the intradiscal space under spinal load.

While the diameters of input gear 234, first idler gear 236, second idler gear 238 and output gear 240 are substantially the same in the arrangement shown, it should be appreciated that these diameters are exemplary and may be varied. Similarly, while the number and pitch of teeth in the upper and lower levels of each of input gear 234, first idler gear 236, second idler gear 238 and output gear 240 are the same, these parameters are also exemplary and may be varied. It should be understood that in addition to transferring rotational motion from the power drive 220 of inserter 200 to the drive gear 144 of device 100, linear gear train 222 allows for use of inserter 200 in particular surgical procedures, such as in minimally invasive procedures. For example, in minimally invasive spinal surgery a relatively small incision is made through the skin of the patient for access to the surgical site of the spine. In this type of surgery, steerable expandable interbody fusion device 100 is desirably formed to have a cross-sectional profile as small as practicable for insertion through the incision. This cross section is, in part, determined by the need to pass the distal end of the inserter 200 through the facetectomy (in a TLIF procedure) and further through Kambin's triangle into the disc space. It should be appreciated that the length of this reduced cross section should be sufficient to facilitate rotation of device 100 to a more anterior location within the disc space after insertion. The use of linear gear train 222 allows for both the desired minimal cross-sectional profile and proper length of distal end 208a of housing 208 to at least permit partial entry of distal end 208a through Kambin's triangle in a TLIF procedure. Further details and anatomical dimensions of Kambin's triangle are provided in commonly owned '640 Application identified above.

In furtherance of the construction of inserter 200 for particular use in minimally invasive surgery, the upper and lower levels of input gear 234, first idler gear 236, second idler gear 238 and output gear 240 are spaced to form a passageway 250 to accommodate attachment shaft 118 within the desired cross-sectional profile of housing distal end 208a, as shown in FIGS. 12 and 13. Attachment shaft 218 is supported for rotational movement but not axial movement in housing 208. Attachment shaft 218 includes exterior threads 218a at the distal end that are configured to threadably engage with interior threads 142 of brake 128 for releasable attachment of inserter 200 to device 100. As illustrated in FIG. 13, attachment shaft 218 is positioned in an offset lateral location within housing 208 relative to axles 242, 244, 246 and 248 of gear train 222. In this position, exterior threads 218a of attachment shaft 218 are aligned with interior threads 142 of brake shoe 138 with brake shoe 138 positioned as shown in FIG. 5, wherein first distal end 138a of brake shoe 138 is in contact with first stop surface 143. Proximal end 218b of attachment shaft 218 may be configured to have a complementary shape, such as a square or hexagonal configuration, for detachable connection to a suitable tool to rotate attachment shaft 218 for threaded attachment to brake 128.

While device 100 may be constrained relative to inserter 200 for expansion upon contact of brake shoe 138 with a stop surface as described above, device 100 is also configured for and capable of constraint relative to inserter 200 by application of brake 128 in curved path 132. To apply brake 128 and constrain device 100 relative to inserter 200 in any position within curved path 132, attachment shaft 218 is rotated in a clockwise direction to fully tighten the threaded connection between exterior threads 218a of attachment shaft 218 and interior threads 142 of brake 128. Such tightening will securely clamp front wall 112e of center body 112 between brake shoe 138 and a curved distal end surface 208b of inserter 200 (see FIGS. 11 and 13) thereby constraining device 100 from rotational movement relative to inserter 200 in both the first direction and opposite second direction. Appropriate tightening and constraint against movement of device 100 can be determined tactilely by the surgeon. As so constrained, device 100 may be expanded within the disc space by rotation of drive shaft 212 in a counterclockwise direction to cause rotation of drive gear 144 in the opposite second direction to actuate expansion mechanism 126 and expand device 100 as described above.

It should be understood, however, that apparatus 10 as described herein may be used in spinal interbody fusion surgery to introduce a steerable expandable interbody fusion device 100 in other than in minimally invasive procedures. In an open procedure, for example, surgical instruments may be used with less consideration for size. In this regard, inserter 200 may be modified to either reduce the number of gears in gear train 222 or to eliminate the gear train 222 completely. With gear train 222 eliminated, power drive 220 may be supported in inserter housing 208 such that spur gear 228 intermeshes directly with drive gear 144. In applications where the gear train 222 may be included, the number of gears may be suitably increased or decreased to suit the application. In addition, gears having a single level of teeth rather than upper and lower levels may also be used in gear train 222, as well as in drive gear 144.

The steerable expandable interbody fusion device 100 may be formed to have a substantially parallelepiped configuration having a fixed length in the range of 20-70 mm, a fixed width in the range of 8-30 mm, an unexpanded height in the range of 6-10 mm and be capable of expanding in the range of 2-7 mm in the height direction. In the exemplary arrangement of steerable expandable interbody fusion device 100 that is configured for use in a minimally invasive transforaminal lumbar interbody fusion (TLIF) procedure, device 100 may be formed to have a fixed length of 27 mm, a fixed width of 10 mm and an unexpanded height of 8 mm. Upon expansion the height of device 100 may be increased to 14 mm.

All of the components of steerable expandable interbody fusion device 100, except for belt 174 of power transmission band 148, may be formed of suitable biocompatible metallic materials, such as pure titanium, tantalum, cobalt-chromium alloys, titanium alloys (e.g., nickel titanium alloys and tungsten titanium alloys), stainless steel alloys, and molybdenum rhenium. In addition any of the following polymeric materials may be used: members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers. It should be appreciated that these materials may be used independently or in a composite arrangement, as desired.

Figure 15:
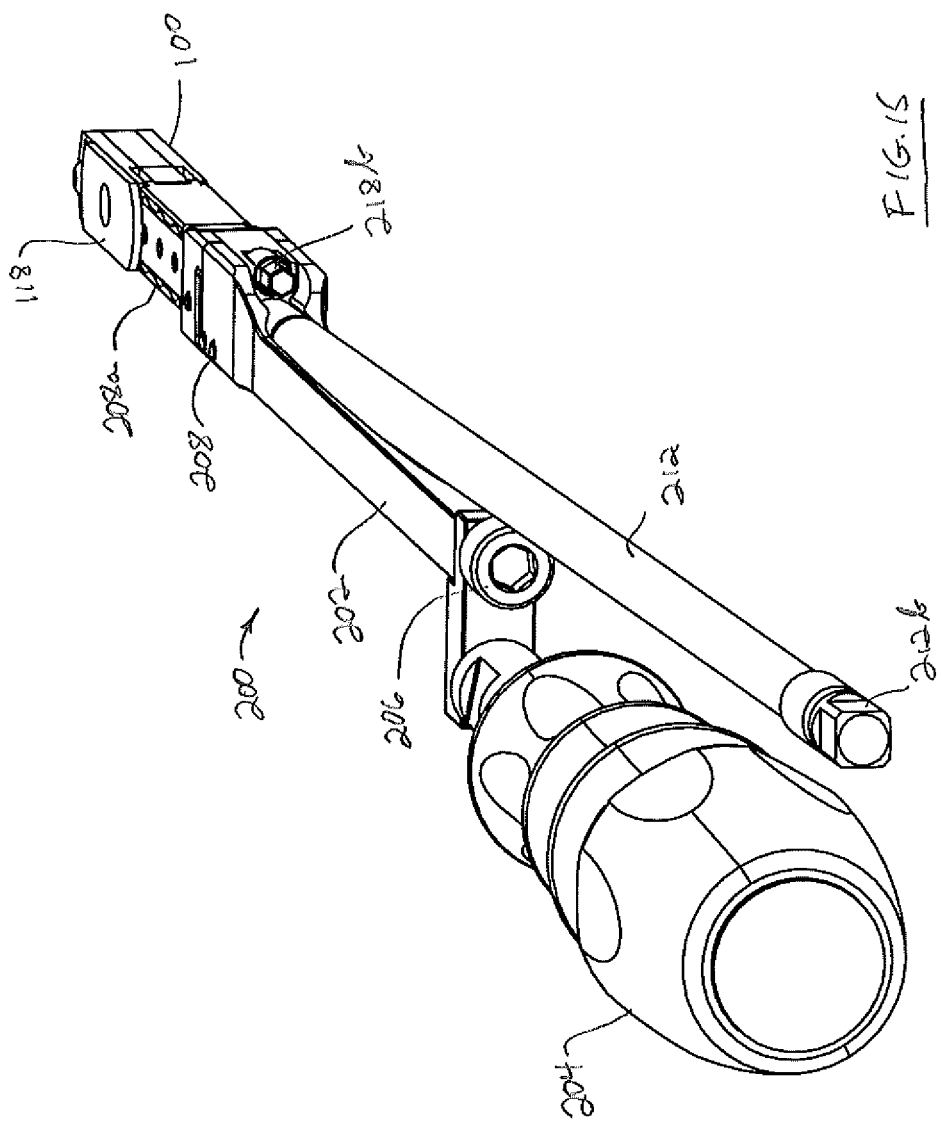
FIG. 15 is a top perspective view of the apparatus of FIG. 1 comprising the steerable expandable interbody fusion device attached to the associated inserter, with the subject steerable expandable interbody fusion device being unexpanded and oriented in a colinear position relative to the subject inserter.

Having described the details of apparatus 10 comprising steerable expandable interbody fusion device 100 and associated inserter 200 the use of apparatus 10 in an exemplary spinal interbody fusion surgical procedure is described. In accordance with a particular arrangement, device 100 and instrument 200 are sized and configured for introducing device 100 in a posterolateral approach in a minimally invasive transforaminal lumbar interbody fusion (TLIF) procedure through a small incision of about 25-50 mm in length through the skin of a patient. The disc space to be treated is appropriately prepared for introduction of device 100. Inserter 200 is appropriately attached to device 100 by aligning exterior threads 218a of attachment shaft 218 with interior threads 142 of brake shoe 138 supported by center body 112 in the position shown in FIG. 5. Attachment shaft 218 is rotated clockwise at its proximal end 218b by a suitable tool to threadably engage exterior threads 218a with interior threads 142 of brake shoe 138. During attachment, upper stabilizing tabs 214a and 214b and lower stabilizing tabs 216a and 216b will respectively enter upper space 180 and lower space 182 of device 100 to hold and stabilize device 100 and inserter 200 in a fixed position. Attachment shaft 218 is rotated to provide sufficient force as determined tactilely by the surgeon to hold device 100 and inserter 200 together while not constraining brake shoe 138 from moving within curved path 132 in center body 112, as described above. Upon attachment of attachment shaft 218 to brake 128, brake shoe 138 is maintained in a fixed position relative to inserter 200. Since brake shoe 138 is configured to move within curved path 132 of device 100 unless constrained, device 100 may rotate on brake shoe 138 about center point 132a relative to inserter 200. In this attached position, device 100 is unexpanded and substantially colinearly aligned with elongate tubular body 202 of instrument 200, as shown in FIG. 15.

Using inserter handle 204, the surgeon manually introduces unexpanded device 100 and at least a portion of distal end 208a through the formed incision into the disc space between two opposing vertebral bodies. During introduction, unexpanded device 100 may be constrained if desired by fully applying brake 128 as described above to prevent unwanted movement. Alternatively, unexpanded device 100 maybe left unconstrained and allowed to passively rotate during insertion. Once introduced into the disc space with unexpanded device 100 still being colinear relative to inserter 200 as depicted in FIG. 15, the surgeon may, if desired, expand device 100 without applying brake 128 since device 100 is constrained against rotational movement in the opposite second direction by the first stop surface 134.

Figure 16:
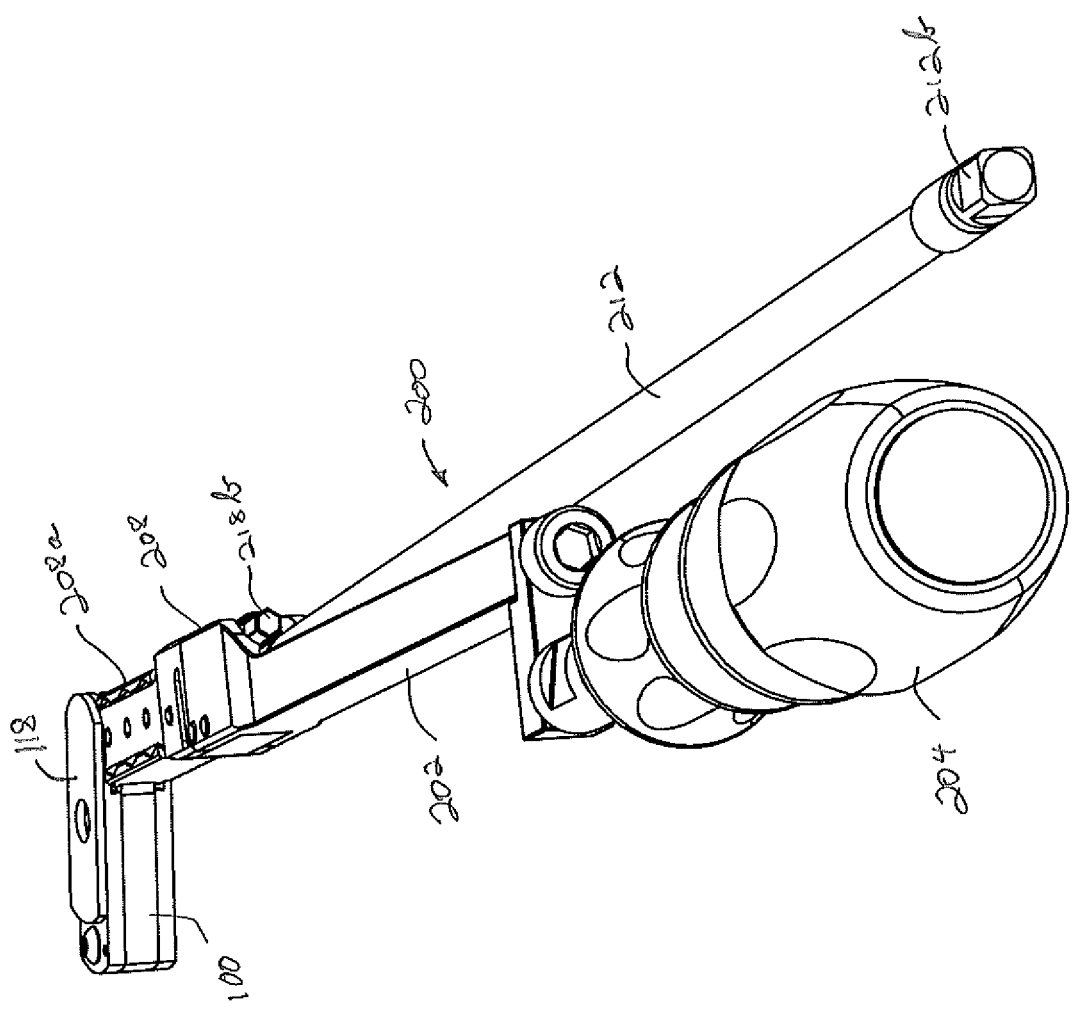
FIG. 16 is the perspective view of the apparatus of FIG. 1 with the subject steerable expandable interbody fusion device being in an unexpanded condition.

If no expansion is desired upon initial introduction, manual introduction continues until a location within the disc space is reached that the surgeon considers appropriate for rotation of the device 100 to a more desirable anterior position. If brake 128 was applied for insertion, it should be released at this point by loosening attachment shaft 218 slightly. At this point, the surgeon may steer unexpanded device 100 medially and preferably across the patient's midline to the desired anterior position. Steering is accomplished by rotating drive shaft 212 in a clockwise direction with a suitable tool to actuate power drive 220, thereby causing rotation of the gears of gear train 222 with output gear 240 ultimately rotating drive gear 144 of device 100 in the first direction. With brake shoe 138 permitted to move within curved path 132 of center body 112, rotation of drive gear 144 will simultaneously rotate device 100 on brake shoe 138 in the first direction about center 132a, in the first mode of operation described above. Such rotation of drive shaft 212 to rotate device 100 may continue until opposite second end 138b of brake shoe 138 comes into contact with second stop surface 136, as illustrated in FIG. 5, thereby constraining further movement of brake shoe 138 within curved path 132. Upon reaching this position, device 100 in this exemplary arrangement, would have traversed an arcuate path of approximately 80° from its initial position of FIG. 15 to its fully rotated position as shown in FIG. 16. At this point, further rotation of device 100 in the first direction is constrained relative to inserter 200 by second stop surface 136.

Figure 17:
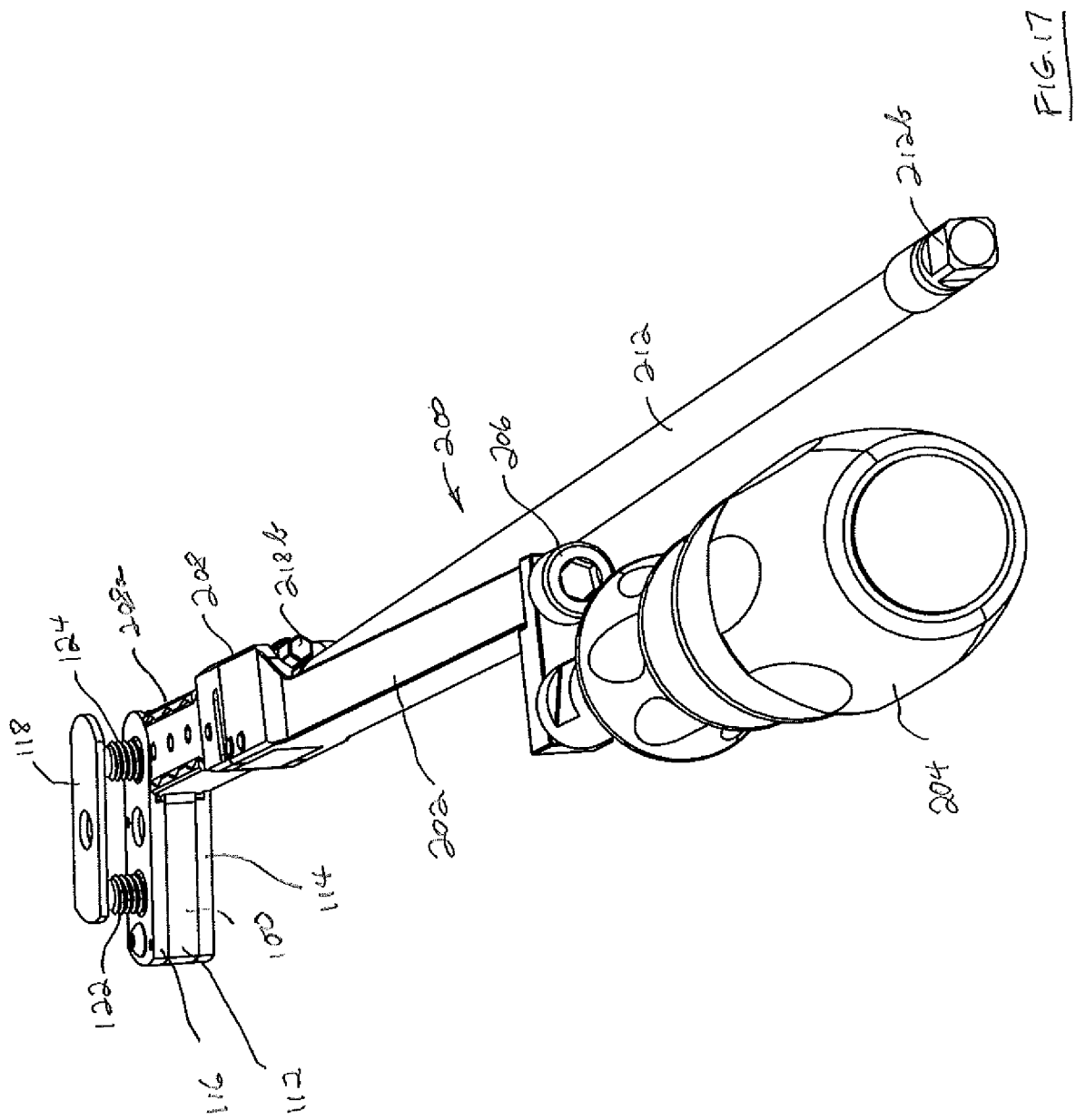
FIG. 17 is a top perspective view of the apparatus of FIG. 1 as seen from a different perspective angle.

Once in the position shown in FIG. 16, brake 128 may be applied as described above to allow for expansion of device 100 within the disc space to the position shown in FIG. 17 (the same position as illustrated in FIG. 1). Thereafter, rotation of drive shaft 212 in the opposite counterclockwise direction will in the second mode of operation actuate expansion mechanism 126 causing drive gear 144 to rotate on lower plate 114 about axis 156 in the opposite second direction. Such rotation of drive gear 144 will therefore cause movement of power transmission band 148 and hence simultaneous rotation of spindle 146. Simultaneous rotation of drive gear 144 and spindle 146 in the same direction will cause upward telescoping movement of threaded posts 122 and 124 within spindle 146 and drive gear 144, respectively. Such telescoping movement of threaded post 122 and 124 will lift movable endplate 118 upwardly away from upper plate 116 to thereby increase the height of device 100 and restoration of the disc height.

Upon completion of insertion and expansion of device 100, inserter 200 may then be released from device 100. Detachment is effected by counterclockwise rotation of attachment shaft 218 with a suitable tool attached to proximal end 218b. Such rotation continues until exterior threads 218a of attachment shaft 218 are separated from interior threads 142 of brake shoe 138 at which point inserter 200 may be withdrawn from the surgical site. Suitable graft material may be pre-packed into the device 100 prior to introduction and post-packed directly into the disc space and between the movable endplate 118 and upper plate 116 after expansion of device 100 and removal of inserter 200. It should be understood that as used herein, terms such as "clockwise" and "counterclockwise" are relative terms that are not intended to be limiting.

With reference now to FIGS. 18-21, a second embodiment of an expandable interbody fusion device 300 is described. Similar to device 100, expandable device 300 is a spinal implant that is particularly configured for use as a TLIF device. Device 300 may likewise be introduced in other approaches, such as in the posterior direction at different levels of the spine, in the oblique anterior/lateral direction (OLIF), or in open surgical procedures.

With further reference to FIGS. 18-21, details of expandable interbody fusion device 300 are described. Device 300 comprises a hollow body 312, a lower endplate 314, an upper endplate 316. In this particular arrangement, lower endplate 314 may be fixed to body 312 and upper endplate 316 is movable upwardly relative to body 312 such that that upon movement the height of device 300 expands. Movable upper endplate 316 includes a top surface 316a that is configured for contact with an endplate of a first vertebral body that communicates with the disc space to be treated. Similarly, lower plate 314 includes a bottom surface 314a configured for contact with an endplate of a second opposing vertebral body that communicates with the disc space to be treated. Upper endplate 316 may have an opening 316b formed therethrough in communication with the interior of hollow body 312 to facilitate fusion of bone graft within device 300 to first vertebral body. Lower plate 314 may also have a similar opening 314b (FIG. 20) therethrough to facilitate fusion of bone graft with a second opposing vertebral body. An opening 335 is formed through a side wall 337 of body 312, side opening 335 being in communication with lower opening 314b and upper opening 316b. Top surface 316a and bottom surface 314a may each be suitably roughened to have a textured surface to facilitate microintegration of device 300 with the respective vertebral bodies to promote fusion with device 300 similar to the textured surfaces as described above with respect to device 100.

Movement of movable upper endplate 316 is effected by threaded telescoping posts 322 and 324 that are each respectively fixedly attached to a bottom surface 316c of movable endplate 316. Threaded post 322 is located adjacent to a distal end 300a of device 300 and threaded post 324 is located adjacent to a proximal end 300b of device 300. Actuation of an expansion mechanism 326 (FIG. 21) causes telescoping movement of threaded posts 322 and 324, as will be explained.

Figure 18:
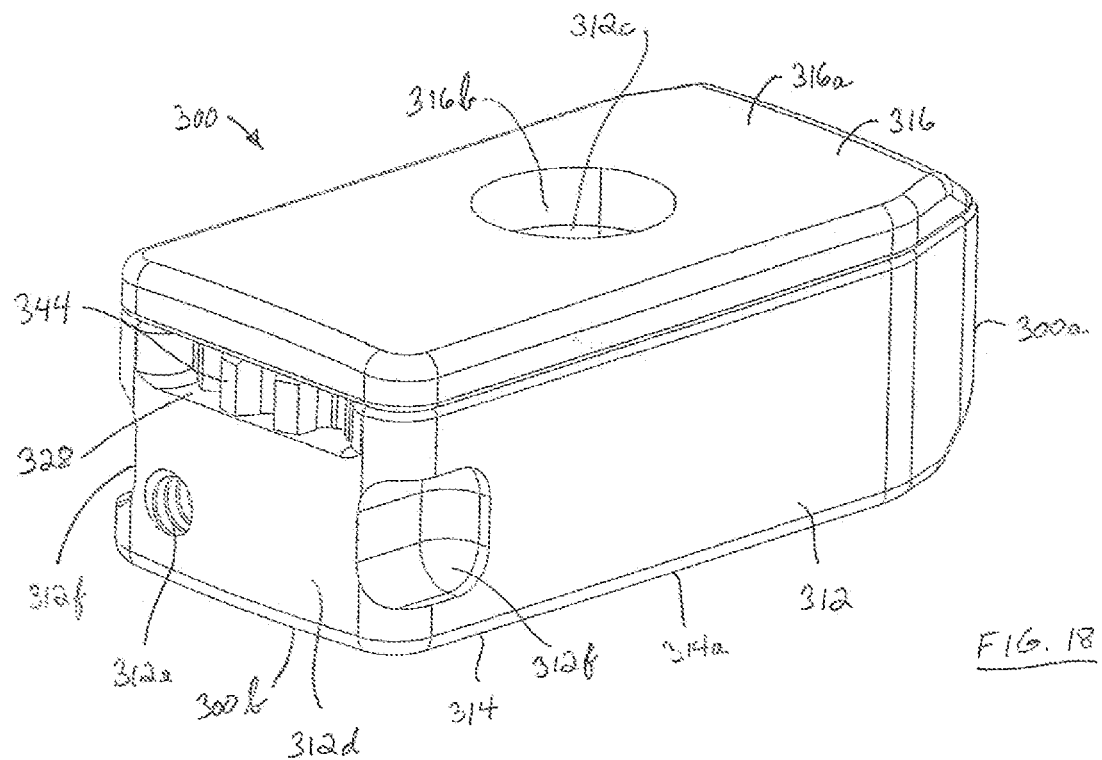
FIG. 18 is a top perspective view of an apparatus for use in spinal interbody fusion surgery according to a second embodiment of the invention with the subject expandable interbody fusion device being shown in an unexpanded condition.
Figure 19:
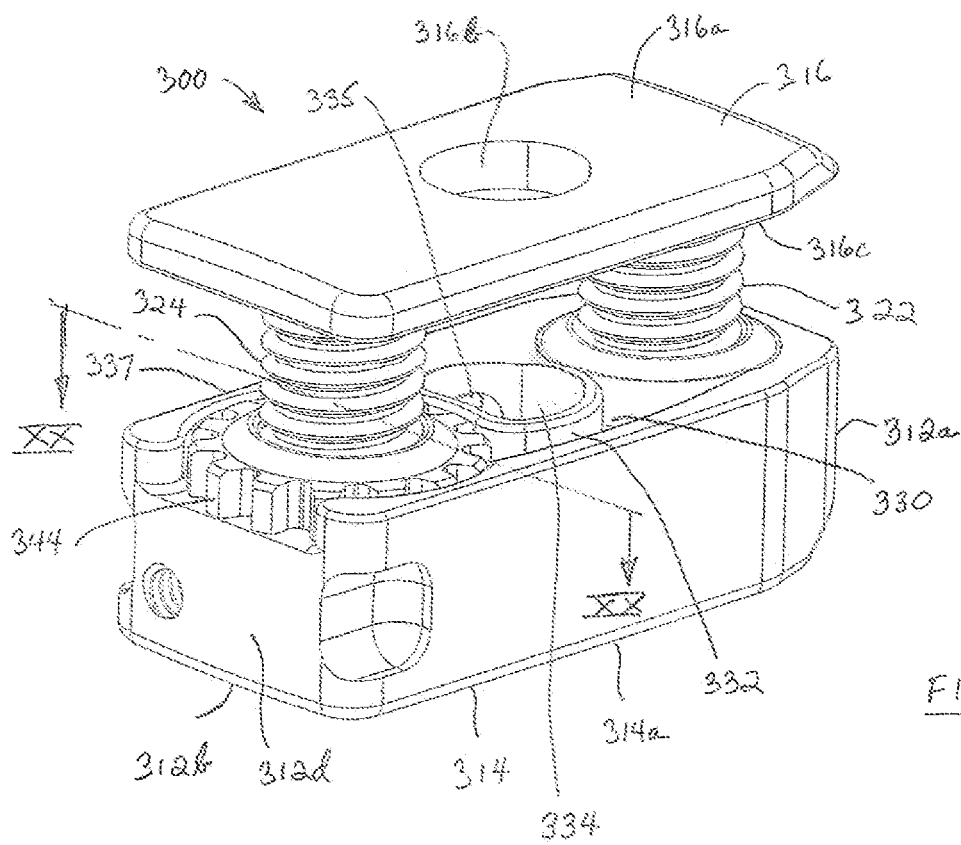
FIG. 19 is a perspective view of the expandable interbody fusion device of FIG. 18 shown in an expanded condition.
Figure 20:
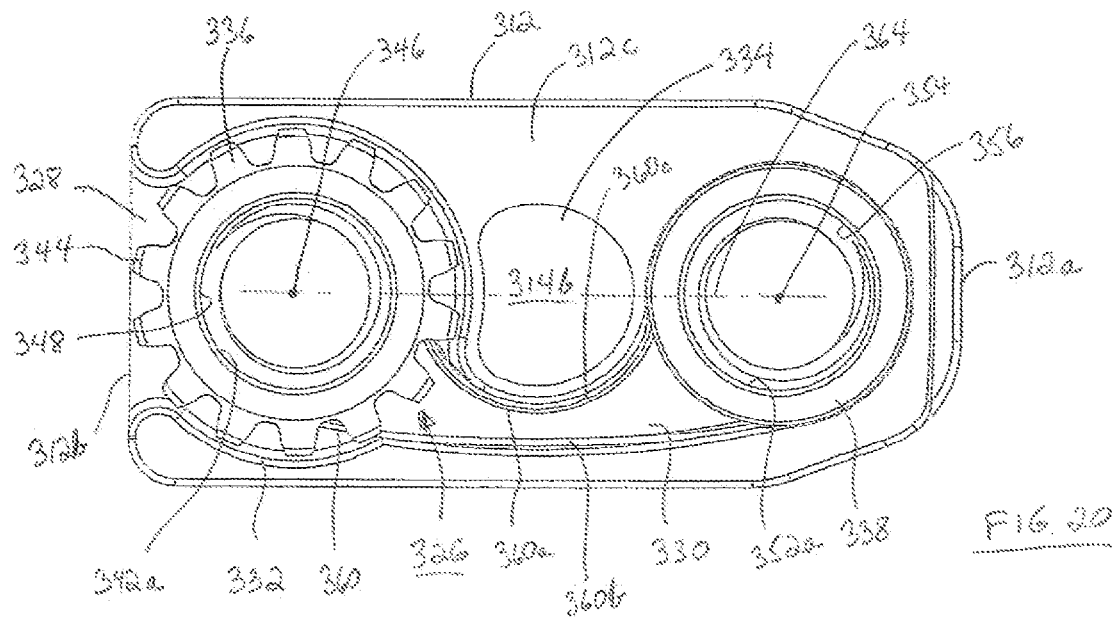
FIG. 20 is a cross-sectional view of the expandable device as seen along viewing line XX-XX of FIG. 19.

Details of the hollow body 312 are now described. As illustrated in FIGS. 18, 19 and 20, body 312 has a distal end 312a, a proximal end 312b and a hollow interior 312c. Proximal end 312b of body 312 includes a front wall 312d having an access window 328 extending therethrough in communication with hollow interior 312c, the purpose of which will be described. A front wall 312d includes a threaded opening 312e for connection to a threaded portion of an insertion instrument for use in introducing device 300 into an intravertebral disc space. Additionally, body 312 includes a pair of notches 312f at proximal end 312b that are configured to receive portions of the insertion instrument to facilitate stabilization of device 300 into the disc space during introduction. Body 312 further includes within hollow interior 312c a pocket 330 defined by a curved interior wall 332 that is configured to snake within hollow interior 312c around opening 314b that extends through lower plate 314. As shown particularly in FIG. 20, pocket 330 has a generally kidney-shaped configuration. Wall 332 separates pocket from a graft chamber 334 disposed within hollow interior 312c, graft chamber 334 being in communication with lower opening 314b, upper opening 316b and side opening 335. Expansion mechanism 326 is fully contained within pocket 330, as illustrated in FIGS. 19 and 20, and separated from graft chamber 334.

Figure 21:
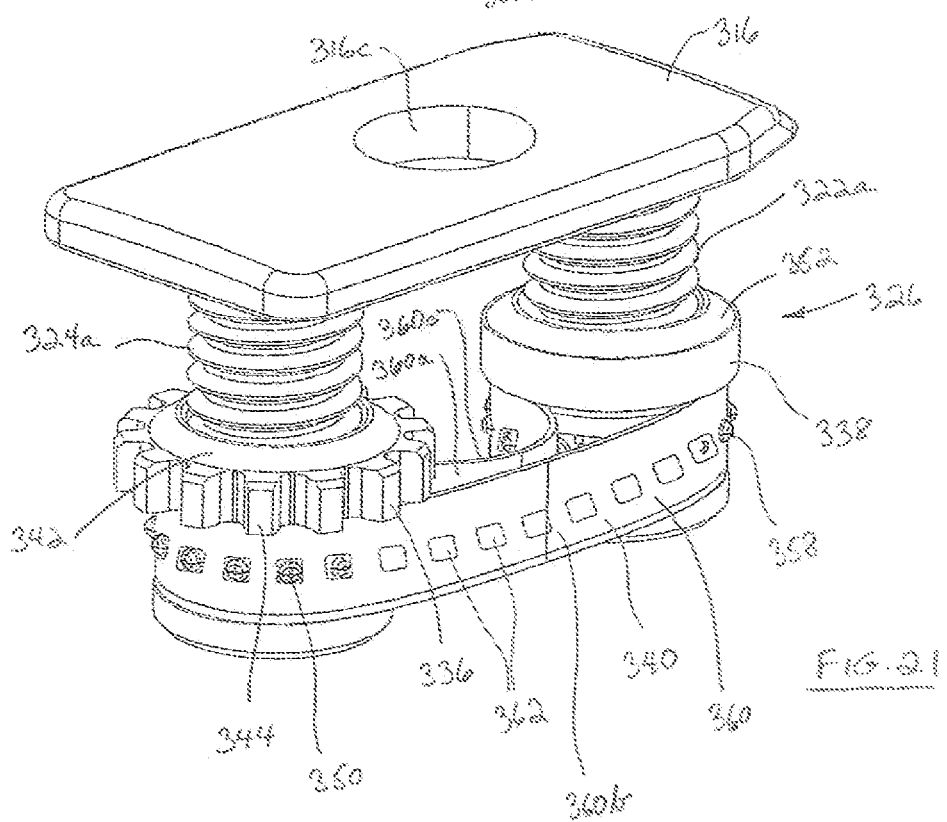
FIG. 21 is a view of the expanded device of FIG. 19 with the body removed to show details of the expansion mechanism for increasing the height of the expandable interbody fusion device.

Turning now to FIG. 21 further details of expansion mechanism 326 are described. Expansion mechanism 326 comprises a drive gear 336, a spindle 338, which serves as a follower of drive gear 336, and a power transmission band 340 that couples drive gear 336 and spindle 338. Power transmission band 340 transfers rotative motion from drive gear 336 to spindle 338, as will be described. Drive gear 336 comprises a generally cylindrical central hub 342 supporting a plurality of gear teeth 344 projecting radially outwardly from hub 342. Gear teeth 344 are configured on central hub 342 to be accessible though body window 328 (see FIG. 18) to mesh with gears of an inserter to actuate expansion mechanism 326 upon introduction of device 300 into the disc space. As shown in FIGS. 19 and 20 drive gear 336 is supported by body 312 at the proximal end 312b for rotation thereon about a central axis 346. Hub 342 has a central opening 342a that includes interior threads 348 to threadably interengage with exterior threads 324a of threaded post 324 that is fixedly attached to movable endplate 316. Disposed adjacent the lower portion of hub 342 below gear teeth 344 is a set of motion transfer teeth 350 that extend circumferentially around and project radially outwardly from hub 342. Motion transfer teeth 350 are configured to mesh with power transmission band 340, as will be described.

Referring still to FIG. 21, spindle 338 comprises a generally cylindrical central hub 352. Central hub 352 has a diameter approximately the same as the diameter of central hub 342 of drive gear 336. As shown in FIGS. 19 and 20, spindle 338 is supported by body 312 at the distal end 312a for rotation thereon about a central axis 354. Central hub 352 has a central opening 352a that includes interior threads 356 to threadably interengage with exterior threads 322a of threaded post 322 that is fixedly attached to movable endplate 316. Disposed adjacent the lower portion of hub 352 is a set of motion transfer teeth 358 that extend circumferentially around and project radially outwardly from central hub 352. Motion transfer teeth 358 are configured to mesh with power transmission band 340. The pitch of motion transfer teeth 358 of spindle 338 is substantially the same as the pitch of motion transfer teeth 350 of drive gear 336.

Referring yet to FIG. 21, power transmission band 340 is formed of a transmission belt 360 of metal. formed in a continuous loop extending around drive gear 336 and spindle 338. In a particular exemplary arrangement, belt 360 is comprised of nitinol, although other suitable biocompatible materials having sufficient elastic properties and strength characteristics may be used. A plurality of belt teeth openings 362 are formed through belt 360 along its entire length. Belt openings 362 are spaced at a distance substantially equal to the pitch of motion transfer teeth 350 of drive gear 336 and motion transfer teeth 358 of spindle 338 such that motion transfer teeth 350 and 358 respectively extend through and intermesh with belt openings 362. Accordingly, upon rotational movement of drive gear 336 by a gear of a suitable insertion instrument to actuate expansion mechanism 326, motion is transferred from drive gear 336 through belt 360 to spindle 338 thereby causing rotation of spindle 338 at approximately the same rate as the rotation of drive gear 336. It should be understood that other structure for coupling belt 360 with drive gear 336 and spindle 338 may be used.

Referring now again to FIGS. 20 and 21, the assembly of expansion mechanism 326 to body 312 is described. Expansion mechanism 326 is disposed within pocket 330 such that drive gear 336 is located adjacent proximal end 312b and gear teeth 344 are exposed through window 328 extending through front wall 312d. Spindle 338 is disposed adjacent distal end 312a of body 312 on the opposite side of lower opening 314b. Transmission belt 360 directly couples drive gear 336 and spindle 338 and extends within pocket 330 in a continuous loop in an oblong shape around drive gear 336 and spindle 336. As such, transmission belt 360 follows the path of pocket 330 established by interior wall 332, as described above. As so disposed, the continuous loop of belt 360 includes a first side 360a and a second side 360b extending between drive gear 336 and spindle 338. First side 360a has an inward curve 360c between drive gear 336 and spindle (see FIG. 21) that circumvents graft chamber 330. In this disposition, both second side 360b and inward curve 360c of first side 360a lie on the same side of a line 364 connecting axis 346 of drive gear 336 and axis 354 of spindle 338. Such a disposition of expansion mechanism 326 within pocket 330 allows bone graft material to be post-packed through side opening 335 and into graft chamber 334 with no obstruction by or interference with expansion mechanism 326. As such, graft material can pass freely through upper opening 316c and lower opening 314b for fusing two opposing vertebral bodies. In addition, this construction allows for the use of a belt driven expansion mechanism that facilitates suitable distraction of opposing vertebral bodies under spinal load.

All of the components of expandable interbody fusion device 300 may be formed of the same suitable biocompatible materials as described above with respect to device 100.

While the invention has been illustrated and described in detail in the drawings and foregoing description, the same should be considered as illustrative and not restrictive in character. Accordingly, it is understood that only the preferred embodiments have been presented and that all changes, modifications and further applications that come within the spirit of the invention are desired to be protected.

What is claimed is:

1. An expandable spinal implant, comprising:
   a body having a hollow interior, a proximal end and a distal end, said body supporting an endplate movable relative to said body in a first direction away from said body, and
   an actuatable expansion mechanism within said hollow interior and coupled to said body and said movable endplate to move said movable endplate relative to said body, said expansion mechanism comprising a rotatable drive gear and a rotatable follower supported by said body and spaced from said drive gear, and a transmission belt rotatively coupling said drive gear and said follower to transfer rotative motion from said drive gear to said follower upon actuation of said expansion mechanism, said transmission belt being formed in a continuous loop extending in an oblong shape around said drive gear and said follower and having an inward curve on one side of said loop between said drive gear and said follower.

2. The expandable spinal implant of claim 1, wherein said rotatable drive gear is substantially cylindrical and is supported within said body for rotation thereon.

3. The expandable spinal implant of claim 2, wherein said rotatable drive gear has a central opening with interior threads formed therein.

4. The expandable spinal implant of claim 3, further including an exteriorly threaded telescoping post fixedly attached to a bottom surface of said movable endplate, wherein actuation of expansion mechanism causes telescoping movement of threaded post to move said movable endplate relative to said body in said first direction.

5. The expandable spinal implant of claim 4, wherein said drive gear includes gear teeth projecting radially outwardly, said gear teeth being configured to mesh with gears of an inserter instrument.

6. The expandable spinal implant of claim 4, wherein said drive gear is located adjacent said proximal end of said body and said follower is located adjacent said distal end of said body.

7. The expandable spinal implant of claim 6, further including a second exteriorly threaded telescoping post fixedly attached to said bottom surface of said movable endplate, actuation of expansion mechanism causing cooperative telescoping movement of said second threaded telescoping with said first threaded telescoping post to move said movable endplate relative to said body in said first direction.

8. The expandable spinal implant of claim 7, wherein said body has a graft chamber disposed between said drive gear and said follower extending along said first direction for receiving bone graft material, and wherein said body further has an opening therethrough extending into said graft chamber.

9. The expandable spinal implant of claim 7, wherein said drive gear is rotatable relative to said body about a first central axis that extends along the first direction, and wherein said follower is rotatable relative to said body about a second central axis that extends along the first direction.

10. The expandable spinal implant of claim 9, wherein said continuous loop includes a first side and a second side extending between said drive gear and said follower, said first side containing said inward curve, both said second side and said inward curve of said first side lying on the same side of a line connecting said first central axis and said second central axis.

11. An expandable spinal implant, comprising:
a body having a hollow interior, a proximal end and a distal end, said body supporting an endplate movable relative to said body in a first direction away from said body; and
an actuatable expansion mechanism within said hollow interior and coupled to said body and said movable endplate, said expansion mechanism consisting essentially of:
a substantially cylindrical rotatable drive member supported by and rotatable relative to said body about a first central axis, said rotatable drive member having a central opening with interior threads formed thereon;
an exteriorly threaded telescoping first post in threadable connection with said interior threads of said rotatable drive, said threaded first post being fixedly attached to a bottom surface of said movable endplate;
a substantially cylindrical follower supported by and rotatable relative to said body about a second central axis, said follower being spaced from and coupled to said drive member for rotative transfer of motion from said drive member, said follower having a central opening with interior threads formed thereon;
an exteriorly threaded telescoping second post in threadable connection with said interior threads of said follower, said threaded second post being fixedly attached to a bottom surface of said movable endplate; and
a transmission belt rotatively coupling said drive member and said follower to transfer rotative motion from said drive member to said follower upon actuation of said expansion mechanism;
wherein actuation of said expansion mechanism causes cooperative telescoping movement of said first threaded post and said second threaded post to move said movable endplate relative to said body in said first direction.

12. The expandable spinal implant of claim 11, wherein said drive member is a drive gear including gear teeth projecting radially outwardly, said gear teeth being configured to mesh with gears of an inserter instrument.

13. The expandable spinal implant of claim 12, wherein said drive gear is located adjacent said proximal end of said body and said follower is located adjacent said distal end of said body.

14. The expandable spinal implant of claim 12, wherein said transmission belt is formed in a continuous loop extending in an oblong shape around said drive gear and said follower and having an inward curve on one side of said loop between said drive gear and said follower.

15. The expandable spinal implant of claim 14, wherein said continuous loop includes a first side and a second side extending between said drive gear and said follower, said first side containing said inward curve, both said second side and said inward curve of said first side lying on the same side of a line connecting said first central axis and said second central axis.

16. The expandable spinal implant of claim 11, wherein said transmission belt consists of nitinol.

17. The expandable spinal implant of claim 11, wherein said body has a graft chamber extending into said hollow interior along said first direction for receiving bone graft material, said opening being disposed between said drive gear and said follower.

18. The expandable spinal implant of claim 17, wherein said body includes a curved interior wall curved interior wall defining a pocket that extends around and is separated from said graft chamber, said expansion mechanism being contained within said pocket.

19. The expandable spinal implant of claim 18, wherein said movable endplate has an upper opening extending therethrough, said body has a lower plate having a lower opening extending therethrough, and said body has a side wall having a side opening extending therethrough, said upper opening, said lower opening and said side opening all being in communication with said graft chamber.

20. The expandable spinal implant of claim 11, further including a brake shoe rotatably supported by said body adjacent said proximal end, said brake shoe being rotatable about a center point located within said hollow interior of said body, said brake shoe being selectively operable in a first mode of operation to allow said body to rotate relative to said brake shoe, and in a second mode of operation to constrain movement of said body relative to brake shoe and during such constraint to allow actuation of said expansion mechanism to move said movable endplate relative to said body in said first direction to expand said spinal implant.

21. The steerable expandable spinal implant of claim 20, wherein said body comprises a front wall at said proximal end, said front wall having an interior arcuate surface defining a curved path within which said brake shoe is configured to move.

* * * * *